(12) United States Patent
Lang et al.

(10) Patent No.: US 6,613,102 B2
(45) Date of Patent: *Sep. 2, 2003

(54) COMPOSITION FOR DYEING KERATIN FIBERS WITH A CATIONIC DIRECT DYE AND A THICKENING POLYMER

(75) Inventors: Gérard Lang, Saint Prix (FR); Jean Cotteret, Verneuil sur Seine (FR)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/349,436

(22) Filed: Jul. 8, 1999

(65) Prior Publication Data
US 2003/0005525 A9 Jan. 9, 2003

(30) Foreign Application Priority Data
Jul. 9, 1998 (FR) ............................................ 98.08832

(51) Int. Cl.$^7$ ................................................ A61K 7/13
(52) U.S. Cl. ........................ 8/407; 8/409; 8/426; 8/423; 8/654; 8/561
(58) Field of Search ........................... 8/405, 406, 407, 8/408, 409, 410, 423, 426, 654, 428, 561, 559

(56) References Cited

U.S. PATENT DOCUMENTS

| | | | |
|---|---|---|---|
| 2,798,053 A | 7/1957 | Brown | 521/38 |
| 2,923,692 A | 2/1960 | Ackerman et al. | 524/548 |
| 3,869,454 A | 3/1975 | Lang et al. | 544/105 |
| 3,915,921 A | 10/1975 | Schlatzer, Jr. | 526/238.23 |
| 3,955,918 A | 5/1976 | Lang | 8/426 |
| 3,985,499 A | 10/1976 | Lang et al. | 8/426 |
| 4,025,301 A | 5/1977 | Lang | 534/607 |
| 4,151,162 A | 4/1979 | Lang et al. | 8/405 |
| 4,153,065 A | 5/1979 | Lang | 132/208 |
| 4,168,144 A * | 9/1979 | Curry et al. | 8/426 |
| 4,509,949 A | 4/1985 | Huang et al. | 8/558 |
| 5,131,911 A * | 7/1992 | Lang et al. | 8/405 |
| 5,474,578 A | 12/1995 | Chan et al. | 8/431 |
| 5,685,882 A * | 11/1997 | Samain et al. | 8/408 |
| 5,879,412 A * | 3/1999 | Rondeau et al. | 8/411 |
| 5,919,273 A * | 7/1999 | Rondeau et al. | 8/412 |
| 5,993,490 A * | 11/1999 | Rondeau et al. | 8/409 |
| 6,001,135 A * | 12/1999 | Rondeau et al. | 8/407 |
| 6,010,541 A * | 1/2000 | De la Mettrie et al. | 8/412 |
| 6,045,591 A * | 4/2000 | Deneulenaere | 8/426 |

FOREIGN PATENT DOCUMENTS

| | | |
|---|---|---|
| EP | 0 216 479 | 4/1987 |
| EP | 0 503 853 | 9/1992 |
| EP | 0 714 954 | 6/1996 |
| EP | 756861 * | 2/1997 |
| EP | 0 801 942 | 10/1997 |
| EP | 0 815 828 | 1/1998 |
| EP | 0 827 738 | 3/1998 |
| EP | 0 827 739 | 3/1998 |
| EP | 0 850 636 | 7/1998 |
| EP | 0 850 637 | 7/1998 |
| EP | 0 850 638 | 7/1998 |
| FR | 2 140 205 | 1/1973 |
| FR | 2 189 006 | 1/1974 |
| FR | 2 282 860 | 3/1976 |
| FR | 2 285 851 | 4/1976 |
| FR | 2 416 723 | 9/1979 |
| FR | 2 586 913 | 3/1987 |
| FR | 2 633 940 | 1/1990 |
| FR | 2 751 533 | 1/1998 |
| GB | 1 360 562 | 7/1974 |
| GB | 1 491 930 | 11/1977 |
| GB | 2 142 348 | 1/1985 |
| WO | WO 95/01772 | 1/1995 |
| WO | WO 95/15144 | 6/1995 |
| WO | WO 97/44002 | 11/1997 |
| WO | WO 97/44003 | 11/1997 |

OTHER PUBLICATIONS

CAPLUS printout of RN 12270–13–2, Basic Blue 44 or Maxilon Blue GRL.*
English language Derwent Abstract of EP 0 714 954, Jun. 1996.
English language Derwent Abstract of EP 0 827 738, Mar. 1998.
English language Derwent Abstract of EP 0 827 739, Mar. 1998.
English language Derwent Abstract of EP 0 850 637, Jul. 1998.
English language Derwent Abstract of EP 0 850 638, Jul. 1998.
English language Derwent Abstract of FR 2 416 723, Oct. 1979.
English language Derwent Abstract of FR 2 586 913, Mar. 1987.
English language Derwent Abstract of FR 2 751 533, Jan. 1998.
English language Derwent Abstract of EP 0 815 828, Jan. 1998.
English language Derwent Abstract of EP 0 801 942, Oct. 1997.
English language Derwent Abstract of EP 0 850 636, Jul. 1998.
English language Derwent Abstract of FR 2 633 940, Jan. 1990.

* cited by examiner

*Primary Examiner*—Margaret Einsmann
(74) *Attorney, Agent, or Firm*—Finnegan, Henderson, Farabow, Garrett & Dunner, L.L.P.

(57) ABSTRACT

The invention relates to a composition for dyeing keratin fibers, in particular human keratin fibers such as the hair, comprising at least one cationic direct dye of given formula and at least one thickening polymer chosen from nonionic guar gums, biopolysaccharide gums of microbial origin, gums derived from plant exudates, pectins, alginates, starches, and carboxyalkylcelluloses. The invention also relates to the dyeing processes and dyeing devices using the composition.

42 Claims, No Drawings

COMPOSITION FOR DYEING KERATIN FIBERS WITH A CATIONIC DIRECT DYE AND A THICKENING POLYMER

The invention relates to a composition for dyeing keratin fibers, in particular human keratin fibers such as the hair, comprising, in a medium which is suitable for dyeing, at least one cationic direct dye of given formula and at least one specific thickening polymer. The invention also relates to the dyeing processes and dyeing devices, i.e., kits, using the composition.

Two types of dyeing may be distinguished in the haircare sector. The first is semi-permanent or temporary dyeing, or direct dyeing, which uses dyes capable of giving the hair a natural coloration, a more or less pronounced color change which may withstand shampooing several times. These dyes are also known as direct dyes; they can be used with or without an oxidizing agent. In the presence of an oxidizing agent, the aim is to obtain lightening dyeing. Lightening dyeing is carried out by applying a mixture, prepared at the time of use, of a direct dye and an oxidizing agent to the hair, and makes it possible in particular to obtain, by lightening the melanin in the hair, an advantageous effect such as a unified color in the case of grey hair, or to bring out the color in the case of naturally pigmented hair.

The second is permanent dyeing or oxidation dyeing. This is carried out with so-called "oxidation" dyes comprising oxidation dye precursors and couplers. Oxidation dye precursors, commonly known as "oxidation bases", are compounds which are initially colorless or weakly colored which develop their dyeing power on the hair in the presence of oxidizing agents added at the time of use, leading to the formation of colored compounds and dyes. The formation of these colored compounds and dyes results either from an oxidative condensation of the "oxidation bases" with themselves or from an oxidative condensation of the oxidation bases with coloration-modifying compounds commonly known as "couplers", which are generally present in the dye compositions used in oxidation dyeing.

It is known practice to add direct dyes to oxidation dyes in order to vary the shades obtained with the said oxidation dyes or to enrich the shades with glints. Among the cationic direct dyes available in the sector of dyeing keratin fibers, in particular human keratin fibers, the compounds whose structure is developed in the text hereinbelow are already known; nevertheless, these dyes lead to colorations which have characteristics that could still be improved, such as the intensity, the homogeneity of the color distributed along the fiber, in which case the coloration is said to be too selective, and the staying power, in terms of the resistance to the various attacking factors to which the hair may be subjected (light, bad weather, shampooing).

After considerable research conducted in this matter, the present inventors have discovered that it is possible to obtain novel compositions for dyeing keratin fibers which are capable of giving more intense and yet unselective colorations which show good resistance to the various attacking factors to which the hair may be subjected, by combining at least one specific thickening polymer with at least one known cationic direct dye of the prior art, which have the respective formulae defined below. This discovery forms the basis of the present invention.

A first subject of the present invention is thus a composition for dyeing keratin fibers, and in particular human keratin fibers such as the hair, containing, in a medium which is suitable for dyeing, (i) at least one cationic direct dye whose structure corresponds to formulae (I) defined below, characterized in that it also contains (ii) at least one specific thickening polymer.

(i) The cationic direct dye which can be used according to the present invention is a compound of formula (I) below:

$$A-N=N-B \qquad (I)$$

in which:

the symbol A represents a group chosen from the structures $A_1$ to $A_3$ below:

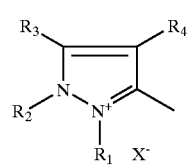

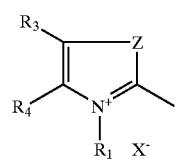

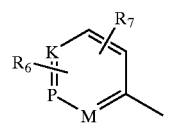

in which structures $A_1$ to $A_3$, $R_1$ denotes a $C_1$–$C_4$ alkyl radical, a phenyl radical which can be substituted with a $C_1$–$C_4$ alkyl radical or a halogen atom chosen from chlorine, bromine, iodine and fluorine;

$R_2$ denotes a $C_1$–$C_4$ alkyl radical or a phenyl radical;

$R_3$ and $R_4$, which may be identical or different, represent a $C_1$–$C_4$ alkyl radical, a phenyl radical or else, in the case of structure A1, can together form a benzene ring substituted with one or more $C_1$–$C_4$ alkyl, $C_1$–$C_4$ alkoxy or $NO_2$ radicals and, in the case of structure A2, can together form a benzene ring optionally substituted with one or more $C_1$–$C_4$ alkyl, $C_1$–$C_4$ alkoxy or $NO_2$ radicals;

$R_3$ can also denote a hydrogen atom;

Z denotes an oxygen or sulphur atom or a group $-NR_2$;

M represents a $-CH$, $-CR$ (R denoting $C_1$–$C_4$ alkyl) or $-N^+R_5(X^-)_r$ group;

K represents a $-CH$, $-CR$ (R denoting $C_1$–$C_4$ alkyl) or $-N^+R_5(X^-)_r$ group;

P represents a $-CH$, $-CR$ (R denoting $C_1$–$C_4$ alkyl) or $-N^+R_5(X^-)_r$ group; r denotes zero or 1;

$R_5$ represents an atom $O^-$, a $C_1$–$C_4$ alkoxy radical or a $C_1$–$C_4$ alkyl radical;

$R_6$ and $R_7$, which may be identical or different, represent a hydrogen atom, a halogen atom chosen from chlorine, bromine, iodine and fluorine, a $C_1$–$C_4$ alkyl or $C_1$–$C_4$ alkoxy radical or an $-NO_2$ radical;

$X^-$ represents an anion preferably chosen from chloride, iodide, methyl sulphate, ethyl sulphate, acetate and perchlorate;

with the proviso that, if $R_4$ denotes a $C_1$–$C_4$ alkyl radical and Z denotes a sulphur atom, $R_3$ does not denote a hydrogen atom;

if $R_5$ denotes $O^-$, then r denotes zero;

if K or P or M denote $C_1$–$C_4$—$N^+$-alkyl $X^-$, then $R_6$ or $R_7$ is other than a hydrogen atom;

if K denotes —$N^+R_5(X^-)_r$, then M=P=—CH, —CR;

if M denotes —$N^+R_5(X^-)_r$, then K=P=—CH, —CR;

if P denotes —$N^+R_5(X^-)_r$, then K=M and denote —CH or —CR;

if Z denotes —$NR_2$ and $R_2$ denotes a $C_1$–$C_4$ alkyl radical, then at least one of the radicals $R_1$, $R_3$ or $R_4$ of the group of structure $A_2$ is other than a $C_1$–$C_4$ alkyl radical;

the symbol B represents:

(a) a group of structure $B_1$ below:

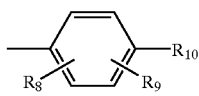

$B_1$ in which structure $B_1$, $R_8$ represents a hydrogen atom, a halogen atom chosen from chlorine, bromine, iodine and fluorine, a $C_1$–$C_4$ alkyl or $C_1$–$C_4$ alkoxy radical, a radical —OH, —$NO_2$, —$NHR_{11}$, —$NR_{12}R_{13}$, —NHCO ($C_1$–$C_4$) alkyl, or forms with $R_9$ a 5- or 6-membered ring which may or may not contain one or more hetero atoms chosen from nitrogen, oxygen and sulphur;

$R_9$ represents a hydrogen atom, a halogen atom chosen from chlorine, bromine, iodine and fluorine, a $C_1$–$C_4$ alkyl or $C_1$–$C_4$ alkoxy radical or forms, with $R_{10}$ or $R_{11}$, a 5- or 6-membered ring which may or may not contain one or more hetero atoms chosen from nitrogen, oxygen and sulphur;

$R_{10}$ represents a hydrogen atom, an —OH radical, a radical —$NHR_{11}$ or a radical —$NR_{12}R_{13}$;

$R_{11}$ represents a hydrogen atom, a $C_1$–$C_4$ alkyl radical, a $C_1$–$C_4$ monohydroxyalkyl radical, a $C_2$–$C_4$ polyhydroxyalkyl radical or a phenyl radical;

$R_{12}$ and $R_{13}$, which may be identical or different, represent a $C_1$–$C_4$ alkyl radical, a $C_1$–$C_4$ monohydroxyalkyl radical or a $C_2$–$C_4$ polyhydroxyalkyl radical;

(b) a 5- or 6-membered nitrogenous heterocyclic group which can contain other hetero atoms and/or carbonyl groups and which can be substituted with one or more $C_1$–$C_4$ alkyl, amino or phenyl radicals, and in particular a group of structure $B_2$ below:

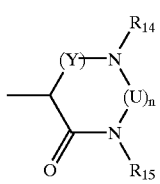

$B_2$ in which structure $B_2$, $R_{14}$ and $R_{15}$, which may be identical or different, represent a hydrogen atom, a $C_1$–$C_4$ alkyl radical or a phenyl radical;

Y denotes the —CO— radical or the radical

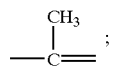

;

n=0 or 1, with, when n denotes 1, U denoting a —CO— radical.

In the structures defined above, the $C_1$–$C_4$ alkyl or alkoxy group preferably denotes methyl, ethyl, butyl, methoxy or ethoxy.

The cationic direct dyes of formula (I) which can be used in the dye compositions in accordance with the invention are known compounds and are described, for example, in patent applications FR-2,189,006, FR-2,285,851 and FR-2,140,205 and its Certificates of Addition, the disclosure of each of which is specifically incorporated by reference herein.

Among the cationic direct dyes of formula (I) which can be used in the dye compositions in accordance with the invention, mention may be made more particularly of the compounds of structures $(I)_1$ to $(I)_{77}$ below:

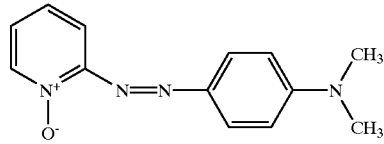

$(I)_1$

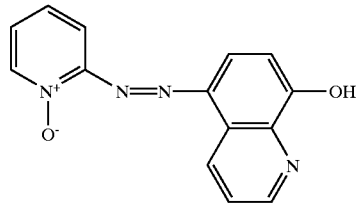

$(I)_2$

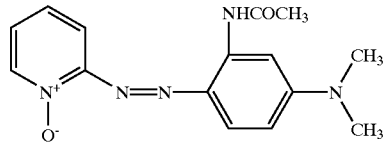

$(I)_3$

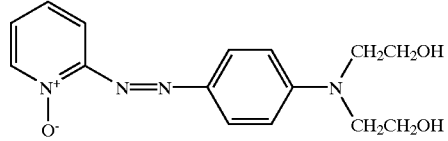

$(I)_4$

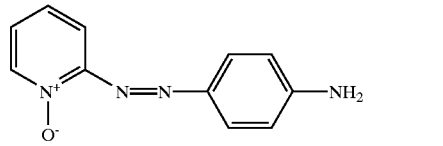

$(I)_5$

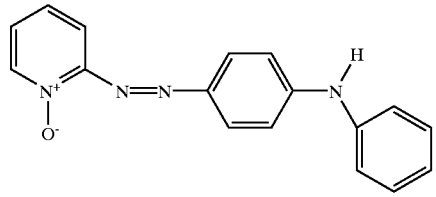

$(I)_6$

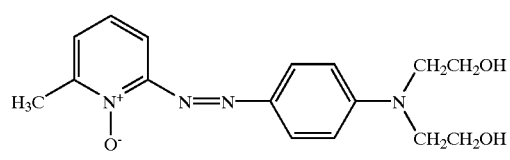
(I)₇
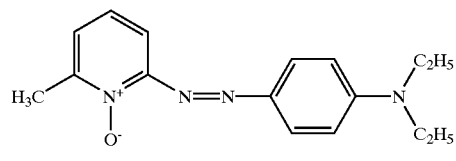
(I)₈
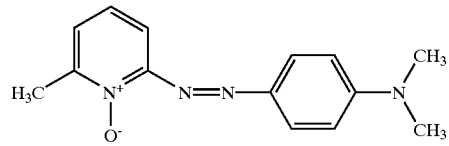
(I)₉
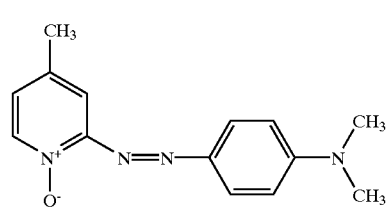
(I)₁₀
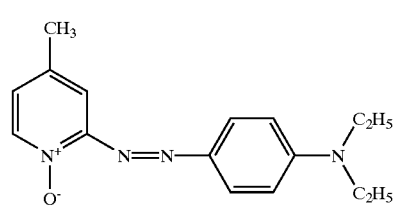
(I)₁₁
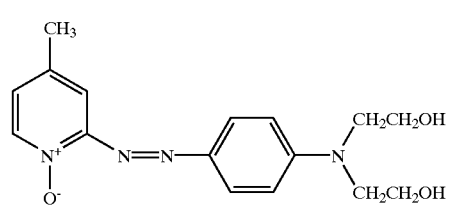
(I)₁₂
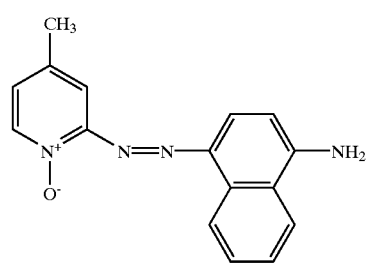
(I)₁₃
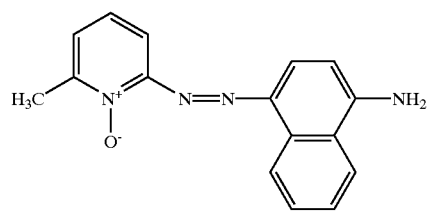
(I)₁₄
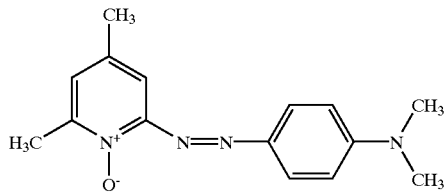
(I)₁₅
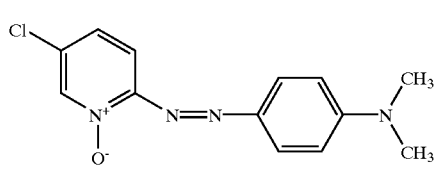
(I)₁₆
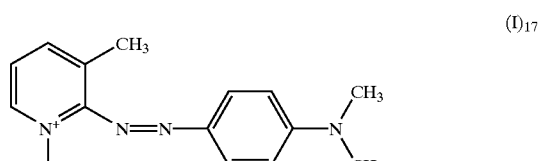
(I)₁₇
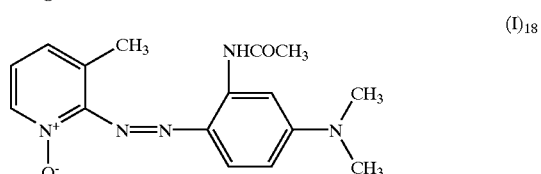
(I)₁₈
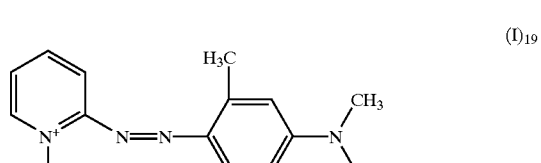
(I)₁₉
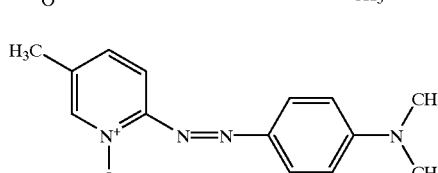
(I)₂₀
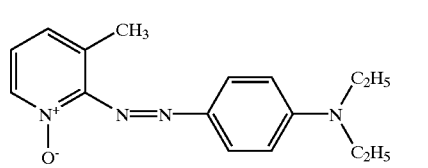
(I)₂₁
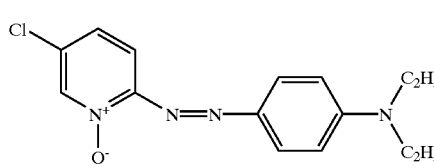
(I)₂₂
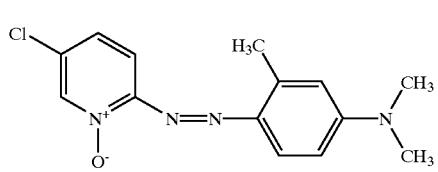
(I)₂₃

-continued (I)₂₄ — 3-methyl-pyridine-N-oxide-2-azo-4'-(N-phenylamino)benzene (I)₂₅ — pyridine-N-oxide-3-azo-4'-(N,N-dimethylamino)benzene (I)₂₆ — pyridine-N-oxide-3-azo-4'-[N,N-bis(2-hydroxyethyl)amino]benzene (I)₂₇ — 1-methylpyridinium-2-azo-4'-(N,N-dimethylamino)benzene, $CH_3SO_4^-$ (I)₂₈ — 1-methylpyridinium-2-azo-4'-aminobenzene, $CH_3SO_4^-$ (I)₂₉ — 1,3-dimethylpyridinium-2-azo-4'-aminobenzene, $CH_3SO_4^-$ (I)₃₀ — 1,4-dimethylpyridinium-2-azo-4'-[N,N-bis(2-hydroxyethyl)amino]benzene, $CH_3SO_4^-$ (I)₃₁ — 1-methylpyridinium-2-azo-4'-(N,N-diethylamino)benzene, $CH_3SO_4^-$ (I)₃₂ — 1,3-dimethylpyridinium-2-azo-4'-(N,N-dimethylamino)benzene, $CH_3SO_4^-$ (I)₃₃ — 1-methylpyridinium-2-azo-(2'-chloro-4'-N,N-dimethylamino)benzene, $CH_3SO_4^-$ (I)₃₄ — 1,6-dimethylpyridinium-2-azo-4'-(N-phenylamino)benzene, $CH_3SO_4^-$ (I)₃₅ — 1,5-dimethylpyridinium-2-azo-4'-(N,N-dimethylamino)benzene, $CH_3SO_4^-$ (I)₃₆ — 1-methylpyridinium-2-azo-(2'-acetamido-4'-N,N-dimethylamino)benzene, $CH_3SO_4^-$ (I)₃₇ — 1-methylpyridinium-3-azo-4'-(N,N-dimethylamino)benzene, $CH_3SO_4^-$ -continued
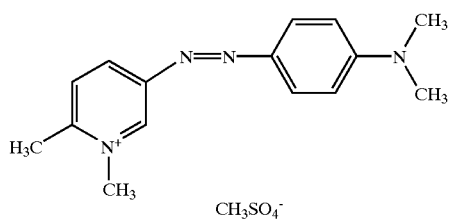
(I)38
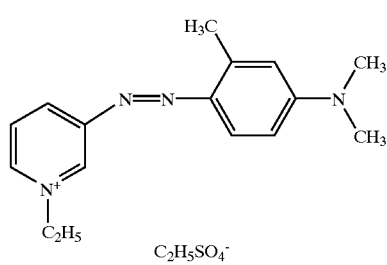
(I)39
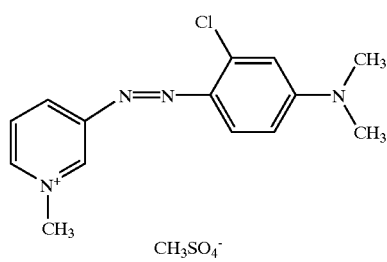
(I)40
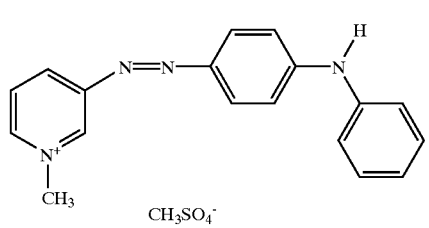
(I)41
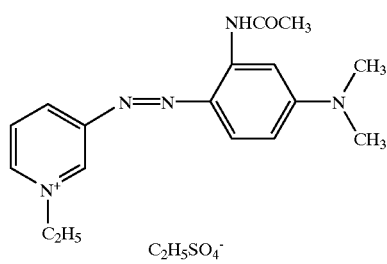
(I)42
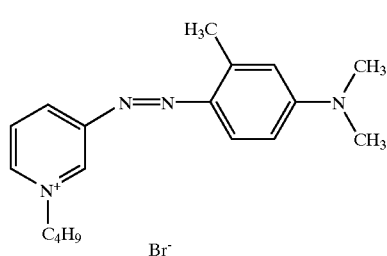
(I)43
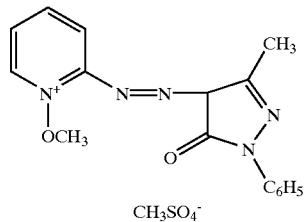
(I)44
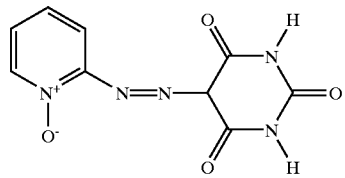
(I)45
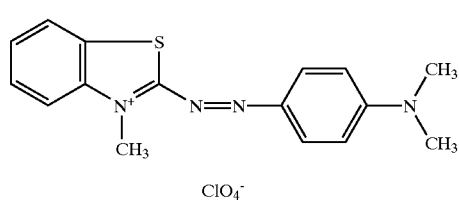
(I)46
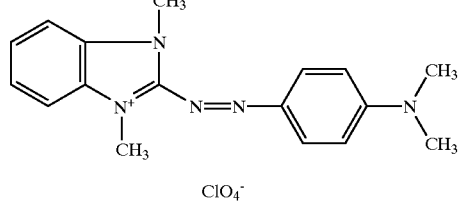
(I)47
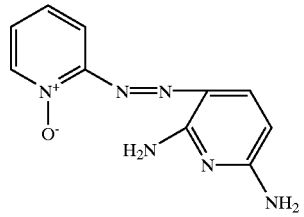
(I)48
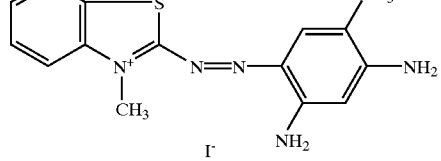
(I)49
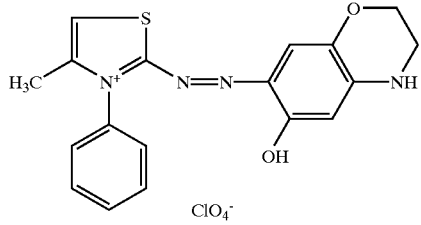
(I)50

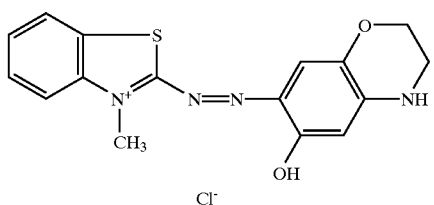 (I)51
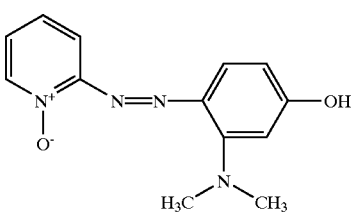 (I)58
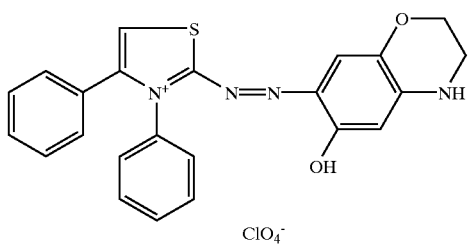 (I)52
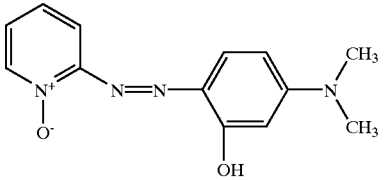 (I)59
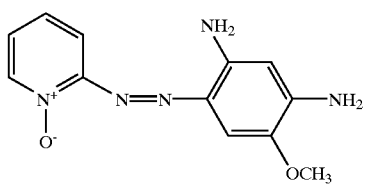 (I)53
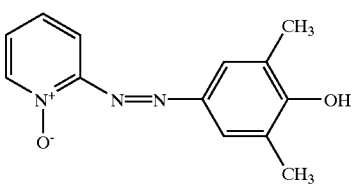 (I)60
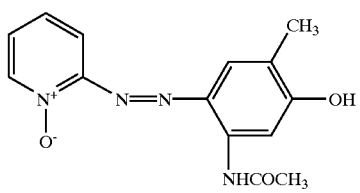 (I)54
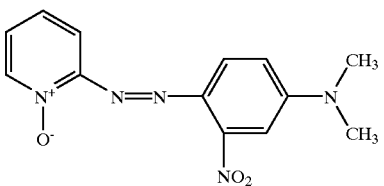 (I)61
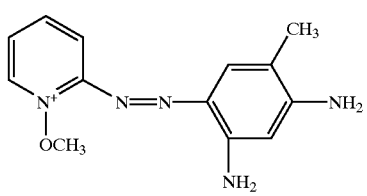 (I)55
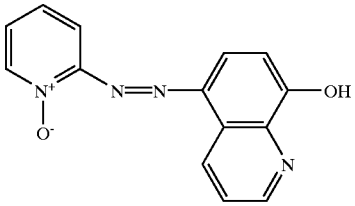 (I)62
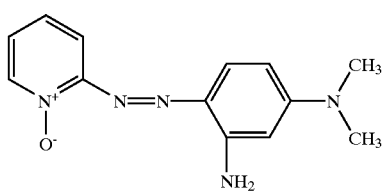 (I)56
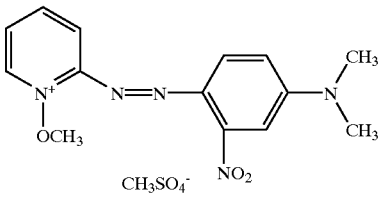 (I)63
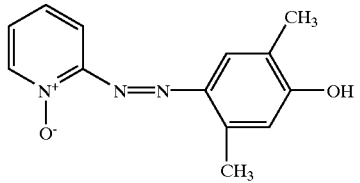 (I)57
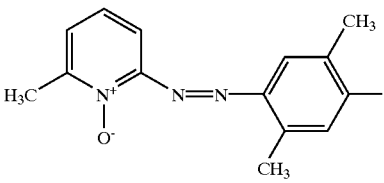 (I)64
(I)65

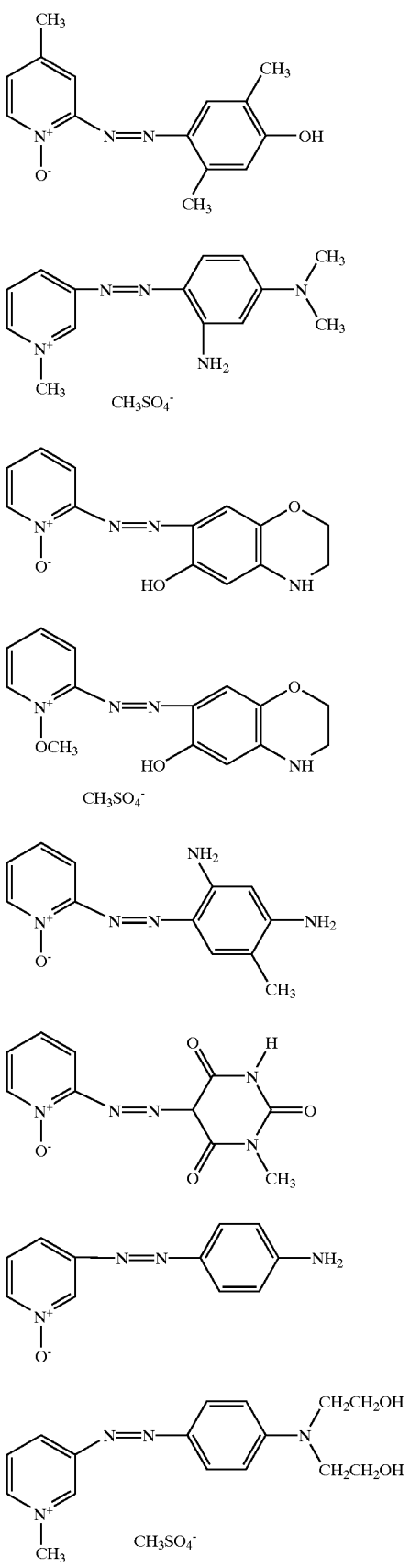
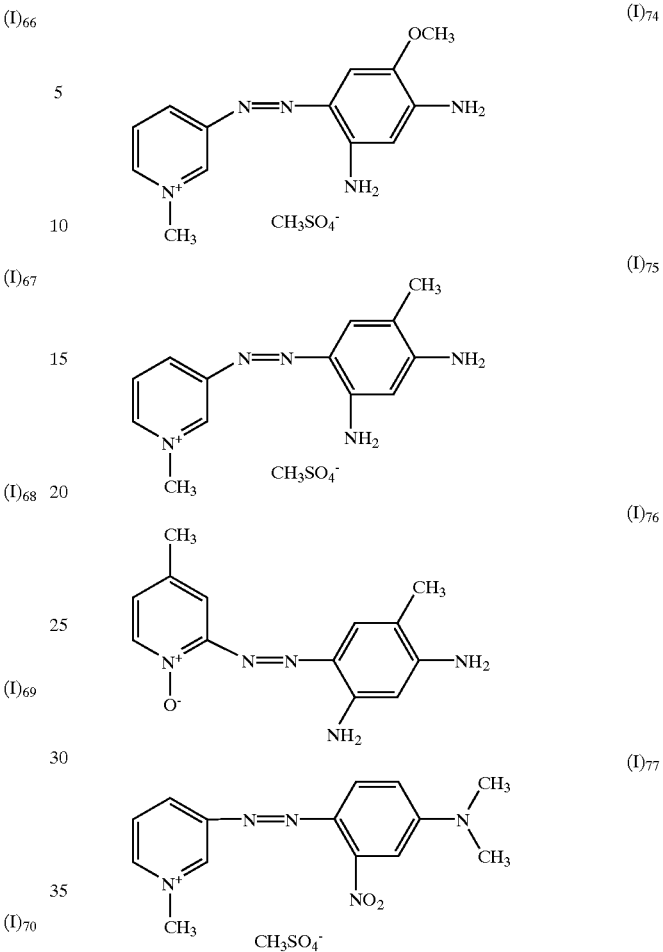

The cationic direct dye(s) of formula (I) used according to the invention preferably represent(s) from 0.001 to 10% by weight approximately relative to the total weight of the dye composition and even more preferably from 0.005 to 5% by weight approximately relative to this weight.

(ii) The thickening polymer which can be used according to the present invention is a polysaccharide or a cellulose chosen from:

(ii)$_1$—nonionic guar gums;
(ii)$_2$—biopolysaccharide gums of microbial origin, such as scleroglucan gum or xanthan gum;
(ii)$_3$—gums derived from plant exudates, such as gum arabic, ghatti gum, karaya gum, gum tragacanth, carrageenan gum, agar gum and carob gum;
(ii)$_4$—pectins;
(ii)$_5$—alginates;
(ii)$_6$—starches;
(ii)$_7$—carboxyalkylcelluloses.

The nonionic guargums can be modified or unmodified. The unmodified guar gums are, for example, the products sold under the name Vidogum GH 175 by the company Unipectine and under the name Jaguar C by the company Meyhall.

According to the present invention, it is preferred to use nonionic guar gums modified with $C_1$–$C_6$ hydroxyalkyl groups.

Among the hydroxyalkyl groups which may be mentioned, for example, are hydroxymethyl, hydroxyethyl, hydroxypropyl and hydroxybutyl groups. These guar gums are well known in the state of the art and can be prepared, for example, by reacting the corresponding alkene oxides such as, for example, propylene oxides, with guar gum so as to obtain a guar gum modified with hydroxypropyl groups. The degree of hydroxyalkylation, which corresponds to the number of alkylene oxide molecules consumed by the number of free hydroxyl functions present on the guar gum, preferably ranges from 0.4 to 1.2.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Rhône-Poulenc (Meyhall) or under the name Galactasol 4H4FD2 by the company Aqualon.

The biopolysaccharide gums of microbial origin, such as scleroglucan gum or xanthan gum, the gums derived from plant exudates such as gum arabic, ghatti gum, karaya gum, gum tragacanth, carrageenan gum, agar gum and carob gum, the hydroxyalkylcelluloses and carboxymethylcelluloses, pectins, alginates and starches are well known to those skilled in the art and are described in particular in the book by Robert L. Davidson entitled "Handbook of Water soluble gums and resins" published by McGraw Hill Book Company (1980), the disclosure of which is specifically incorporated by reference herein.

Among these gums, the scleroglucans more particularly used according to the present invention are represented by the products sold under the name Actigum CS by the company Sanofi Bio Industries and in particular Actigum CS 11, and under the name Amigel by the company Alban Muller International. Other scleroglucans, such as the one treated with glyoxal in French patent application No. 2,633, 940, the disclosure of which is specifically incorporated by reference herein, can also be used.

The xanthan gums more particularly used according to the present invention are represented by the products sold under the names Keltrol, Keltrol T, Keltrol TF, Keltrol BT, Keltrol RD and Keltrol CG by the company Nutrasweet Kelco, or under the names Rhodicare S and Rhodicare H by the company Rhodia Chimie.

Among the carboxyalkylcelluloses preferably used is carboxymethylcellulose, for which mention may be made of the products sold under the names Blanose 7M8/SF, Blanose Raffinée 7M, Blanose 7LF, Blanose 7MF, Blanose 9M31F, Blanose 12M31XP, Blanose 12M31P, Blanose 9M31XF, Blanose 7H, Blanose 7M31 and Blanose 7H3SXF by the company Aqualon, or Aquasorb A500 and Ambergum 1221 by the company Hercules, or Cellogen HP810A and Cellogen HP6HS9 by the company Montello, or Primellose by the company Avebe.

The thickening polymers (ii) used in the compositions of the present invention are preferably present in a proportion of from 0.01 to 10% by weight approximately, in particular in a proportion of from 0.1 to 5% by weight approximately, relative to the total weight of the dye composition applied to the keratin fibers.

The medium which is suitable for dyeing (or support) generally comprises water or a mixture of water and at least one organic solvent to dissolve the compounds which would not be sufficiently water-soluble. As organic solvents, mention may be made, for example, of $C_1$–$C_4$ lower alkanols such as ethanol and isopropanol; aromatic alcohols such as benzyl alcohol, as well as similar products and mixtures thereof.

The solvents can be present in proportions preferably ranging from 1 to 40% by weight approximately relative to the total weight of the dye composition, and even more preferably from 5 to 30% by weight approximately.

The pH of the dye composition in accordance with the invention is generally approximately ranging from 2 to 11 and preferably approximately ranging from 5 to 10. It can be adjusted to the desired value using acidifying or basifying agents usually used for dyeing keratin fibers.

Among the acidifying agents, mention may be made, by way of example, of inorganic or organic acids such as hydrochloric acid, orthophosphoric acid, sulphuric acid, carboxylic acids such as acetic acid, tartaric acid, citric acid and lactic acid, and sulphonic acids.

Among the basifying agents, mention may be made, by way of example, of aqueous ammonia, alkaline carbonates, alkanolamines such as mono-, di- and triethanolamine and derivatives thereof, sodium hydroxide, potassium hydroxide and the compounds of formula (II) below:

(II)

in which W is a propylene residue optionally substituted with a hydroxyl group or a $C_1$–$C_6$ alkyl radical; $R_{16}$, $R_{17}$, $R_{18}$ and $R_{19}$, which may be identical or different, represent a hydrogen atom or a $C_1$–$C_6$ alkyl or $C_1$–$C_6$ hydroxyalkyl radical.

In addition to the cationic direct dye(s) (i) defined above, the dye composition in accordance with the invention can contain one or more additional direct dyes which can be chosen, for example, from nitrobenzene dyes, anthraquinone dyes, naphthoquinone dyes, triarylmethane dyes, xanthene dyes and azo dyes which are non-cationic.

When it is intended for oxidation dyeing, the dye composition in accordance with the invention contains, in addition to the cationic direct dye(s) (i), one or more oxidation bases chosen from the oxidation bases conventionally used for oxidation dyeing and among which mention may be made in particular of para-phenylenediamines, bis(phenyl) alkylenediamines, para-aminophenols, ortho-aminophenols and heterocyclic bases.

When they are used, the oxidation base(s) preferably represent(s) from 0.0005 to 12% by weight approximately relative to the total weight of the dye composition, and even more preferably from 0.005 to 6% by weight approximately relative to this weight.

When it is intended for oxidation dyeing, the dye composition in accordance with the invention can also contain, in addition to the cationic direct dye (i) and the thickening polymer (ii) as well as the oxidation bases, one or more couplers so as to modify the shades obtained or to enrich them with glints, by using the cationic direct dye(s) (i) and the oxidation base(s).

The couplers which can be used in the dye composition in accordance with the invention can be chosen from the couplers used conventionally in oxidation dyeing and among which mention may be made in particular of meta-phenylenediamines, meta-aminophenols, meta-diphenols and heterocyclic couplers.

When it is (they are) present, the coupler(s) preferably represent(s) from 0.0001 to 10% by weight approximately relative to the total weight of the dye composition, and even more preferably from 0.005 to 5% by weight approximately relative to this weight.

The dye composition in accordance with the invention can also contain various adjuvants conventionally used in compositions for dyeing the hair, such as antioxidants, penetrating agents, sequestering agents, fragrances, buffers, dispersing agents, surfactants, film-forming agents, ceramides, preserving agents, screening agents, such as sunscreens, and opacifiers.

Needless to say, a person skilled in the art will take care to select this (these) optional complementary compound(s) such that the advantageous properties intrinsically associated with the dye composition in accordance with the invention are not, or are not substantially, adversely affected by the addition(s) envisaged.

The dye composition according to the invention can be in various forms, such as in the form of liquids, shampoos, creams or gels or any other form which is suitable for dyeing keratin fibers, and in particular human hair. It can be obtained by mixing, at the time of use, a composition, which may be pulverulent, containing the cationic direct dye(s) with a composition containing the specific thickening polymer.

When the combination of the cationic direct dye (i) and the thickening polymer (ii) according to the invention is used in a composition intended for oxidation dyeing (in which case one or more oxidation bases are used, optionally in the presence of one or more couplers) or when it is used in a composition intended for lightening direct dyeing, then the dye composition in accordance with the invention also comprises at least one oxidizing agent chosen, for example, from hydrogen peroxide, urea peroxide, alkali metal bromates, persalts such as perborates and persulphates, and enzymes such as peroxidases, lactases and two-electron oxidoreductases. It is particularly preferred to use hydrogen peroxide or enzymes.

Another subject of the invention is a process for dyeing keratin fibers, and in particular human keratin fibers such as the hair, using the dye composition as defined above.

According to a first variant of this dyeing process in accordance with the invention, at least one dye composition as defined above is applied to the fibers, for a period which is sufficient to develop the desired coloration, after which the fibers are rinsed, optionally washed with shampoo, rinsed again and dried.

The time required to develop the coloration on the keratin fibers is generally from 3 to 60 minutes and even more specifically from 5 to 40 minutes.

According to a second variant of this dyeing process in accordance with the invention, at least one dye composition as defined above is applied to the fibers, for a period which is sufficient to develop the desired coloration, without final rinsing.

According to one specific embodiment of this dyeing process, and when the dye composition in accordance with the invention comprises at least one oxidation base and at least one oxidizing agent, the dyeing process comprises a first step which comprises separately storing, on the one hand, a composition (A1) comprising, in a medium which is suitable for dyeing, at least one cationic direct dye (i) as defined above and at least one oxidation base, and, on the other hand, a composition (B1) comprising, in a medium which is suitable for dyeing, at least one oxidizing agent, and then in mixing them together at the time of use, after which this mixture is applied to the keratin fibers, the composition (A1) or the composition (B1) containing the thickening polymer (ii) as defined above.

According to another specific embodiment of this dyeing process, and when the dye composition in accordance with the invention comprises at least one oxidizing agent, the dyeing process comprises a first step which comprises separately storing, on the one hand, a composition (A2) comprising, in a medium which is suitable for dyeing, at least one cationic direct dye (i) as defined above, and, on the other hand, a composition (B2) comprising, in a medium which is suitable for dyeing, at least one oxidizing agent, and then in mixing them together at the time of use, after which this mixture is applied to the keratin fibers, the composition (A2) or the composition (B2) containing the thickening polymer as defined above.

Another subject of the invention is a multi-compartment dyeing device, i.e., a dyeing "kit" or any other multi-compartment packaging system, a first compartment of which comprises the composition (A1) or (A2) as defined above and a second compartment of which comprises the composition (B1) or (B2) as defined above. These devices can be equipped with means for dispensing the desired mixture onto the hair, such as the devices described in patent FR 2,586,913, the disclosure of which is specifically incorporated by reference herein.

The examples which follow are intended to illustrate the invention without, however, limiting its scope.

EXAMPLES

Examples 1 to 2

The two direct dyeing compositions given in the table below were prepared:

| (all content expressed in grams) | Example 1 | Example 2 |
|---|---|---|
| Cationic direct dye of formula (I)10 | 0.12 | |
| Cationic direct dye of formula (I)27 | | 0.1 |
| Guar gum sold under the name Vidogum GH 175 by the company Unipectine | 1.0 AM* | |
| Scleroglucan gum sold under the name Amigel by the company Alban Muller International | | 1.0 AM* |
| Ethanol | 10 | 10 |
| 2-Amino-2-methyl-1-propanol qs | pH 9 | pH 9 |
| Demineralized water qs | 100 | 100 |

AM* denotes active material

The above compositions were each applied for 30 minutes to locks of natural grey hair containing 90% white hairs. The locks of hair were then rinsed, washed with a strandard shampoo and then dried.

The locks were dyed in the following shades:

| Examples | Shades obtained |
|---|---|
| 1 | Bright red |
| 3 | Bright purple |

What is claimed is:

1. A ready-to-use composition for dyeing keratin fibers comprising:
   (i) at least one cationic dye chosen from compounds of formula (I) below:

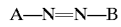

in which:
   the symbol A represents a group chosen from the structures $A_1$ to $A_3$ below:

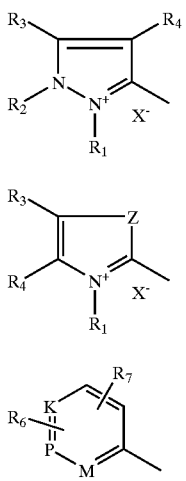

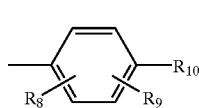

in which structures $A_1$ to $A_3$, $R_1$ is chosen from $C_1$–$C_4$ alkyl radicals, a phenyl radical which can be substituted with a $C_1$–$C_4$ alkyl radical or a halogen atom chosen from chlorine, bromine, iodine and fluorine;

$R_2$ is chosen from $C_1$–$C_4$ alkyl radicals and a phenyl radical;

$R_3$ and $R_4$, which may be identical or different, are chosen from $C_1$–$C_4$ alkyl radicals, a phenyl radical or, together form, in $A_1$, a benzene ring substituted with at least one radical chosen from $C_1$–$C_4$ alkyl radicals, $C_1$–$C_4$ alkoxy radicals and $NO_2$ radicals or, together form, in $A_2$, a benzene ring optionally substituted with at least one radical chosen from $C_1$–$C_4$ alkyl radicals, $C_1$–$C_4$ alkoxy radicals and $NO_2$ radicals;

$R_3$ can be further chosen from a hydrogen atom;

Z is chosen from an oxygen atom, a sulphur atom and —$NR_2$ radicals;

M is chosen from a —CH radical, —$C(C_1$–$C_4$ alkyl) radicals and —$N^+R_5(X^-)_r$ radicals;

K is chosen from a —CH radical, —$C(C_1$–$C_4$ alkyl) radicals and —$N^+R_5(X^-)_r$ radicals;

P is chosen from a —CH radical, —$C(C_1$–$C_4$ alkyl) radicals and —$N^+R_5(X^-)_r$ radicals;

wherein r denotes zero or 1;

wherein $R_5$ is chosen from an $O^-$ anion, $C_1$–$C_4$ alkoxy radicals and $C_1$–$C_4$ alkyl radicals;

$R_6$ and $R_7$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals, and —$NO_2$ radicals;

$X^-$ is chosen from anions;

with the proviso that, wherein if $R_4$ is a $C_1$–$C_4$ alkyl radical and Z denotes a sulphur atom, $R_3$ is not a hydrogen atom;

wherein if $R_5$ is $O^-$, then r is zero;

wherein if K or P or M is —$N^+$—$(C_1$–$C_4$ alkyl)$X^-$, either $R_6$ or $R_7$ is not a hydrogen atom;

wherein if K is —$N^+R_5(X^-)_r$, M and P are the same and are chosen from a —CH radical and —$C(C_1$–$C_4$ alkyl) radicals;

wherein if M is —$N^+R_5(X^-)_r$, K and P are the same and are chosen from a —CH radical and —$C(C_1$–$C_4$ alkyl) radicals;

if P denotes $N^+R_5(X^-)_r$, K and M are the same and are chosen from a —CH radical and —$C(C_1$–$C_4$ alkyl) radicals;

if Z is —$NR_2$ with $R_2$ being a radical chosen from $C_1$–$C_4$ alkyl radicals, at least one of the radicals $R_1$, $R_3$ or $R_4$ of $A_2$ is not chosen from $C_1$–$C_4$ alkyl radicals;

the symbol B is chosen from:

(a) a group of structure $B_1$ below:

$$B_1$$

[structure showing ring with $R_8$, $R_9$, $R_{10}$ substituents]

in which structure $B_1$, $R_8$ is chosen from a hydrogen atom, a halogen atom chosen from chlorine, bromine, iodine and fluorine, $C_1$–$C_4$ alkyl radicals, $C_1$–$C_4$ alkoxy radicals, a radical —OH, a radical —$NO_2$, —$NHR_{11}$ radicals, —$NR_{12}R_{13}$ radicals, —NHCO ($C_1$–$C_4$) alkyl radicals, or forms with $R_9$ a 5- or 6-membered ring which may or may not contain at least one hetero atom chosen from nitrogen, oxygen and sulphur;

$R_9$ is chosen from a hydrogen atom, a halogen atom chosen from chlorine, bromine, iodine and fluorine, $C_1$–$C_4$ alkyl radicals, $C_1$–$C_4$ alkoxy radicals, or forms, with $R_{10}$ or $R_{11}$, a 5- or 6-membered ring which may or may not contain at least one hetero atom chosen from nitrogen, oxygen and sulphur;

$R_{10}$ is chosen from a hydrogen atom, an —OH radical, —$NHR_{11}$ radicals and —$NR_{12}R_{13}$ radicals;

$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;

$R_{12}$ and $R_{13}$, which may be identical or different, are chosen from $C_1$–$C_4$ alkyl radicals, $C_1$–$C_4$ monohydroxyalkyl radicals and $C_2$–$C_4$ polyhydroxyalkyl radicals;

(b) 5- and 6-membered nitrogenous heterocyclic groups optionally containing other heteroatoms or carbonyl groups and optionally substituted with at least one radical chosen from $C_1$–$C_4$ alkyl radicals, an amino radical, a phenyl radical, and (ii) at least one thickening polymer chosen from polymers comprising:

$(ii)_2$—biopolysaccharide gums of microbial origin, except for xanthan gum;

$(ii)_3$—gums derived from plant exudates;

$(ii)_4$—pectins;

$(ii)_5$—alginates; and $(ii)_6$—starches.

2. The composition according to claim 1, wherein said keratin fibers are human keratin fibers.

3. The composition according to claim 2, wherein said human keratin fibers are hair.

4. The composition according to claim 1, wherein in formula (I) the symbol B represents a group of structure of $B_2$ below:

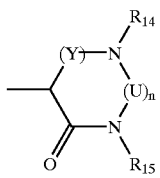

in which structure $B_2$, $R_{14}$ and $R_{15}$, which may be identical or different, are chosen from a hydrogen atom, $C_1$–$C_4$ alkyl radicals and phenyl radicals;

Y is chosen from a —CO— radical and a radical

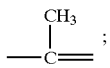

n is 0 or 1, wherein, when n is 1, U is a —CO— radical.

5. The composition according to claim 1, wherein said anions are chosen from chloride, iodide, methyl sulphate, ethyl sulphate, acetate and perchlorate.

6. The composition according to claim 1, wherein in formula (I), the $C_1$–$C_4$ alkyl radicals and the $C_1$–$C_4$ alkoxy radicals are chosen from methyl, ethyl, butyl, methoxy and ethoxy radicals.

7. The composition according to claim 1, further comprising at least one oxidation base that is present in an amount sufficient for lightening direct dyeing.

8. The composition according to claim 1, wherein said at least one cationic dye of formula (I) is present in an amount ranging from 0.001 to 10% by weight relative to the total weight of the composition.

9. The composition according to claim 8, wherein said at least one cationic dye of formula (I) is present in an amount ranging from 0.005 to 5% by weight relative to the total weight of the composition.

10. The composition according to claim 1, wherein said composition further comprises at least one oxidizing agent.

11. The composition according to claim 1, wherein said composition is in a form chosen from a liquid, a shampoo, a cream, and a gel.

12. The composition according to claim 1, wherein said at least one thickening polymer is chosen from biopolysaccharide gums of microbial origin, which are further chosen from scleroglucan gums.

13. The composition according to claim 1, wherein said at least one thickening polymer is chosen from gums derived from plant exudates, which are further chosen from gum arabic, ghatti gum, karaya gum, gum tragacanth, carrageenan gum, agar gum and carob gum.

14. The composition according to claim 1, wherein said at least one thickening polymer is present in an amount ranging from 0.01 to 10% by weight relative to the total weight of the composition.

15. The composition according to claim 14, wherein said at least one thickening polymer is present in an amount ranging from 0.1 to 5% by weight relative to the total weight of the composition.

16. The composition according to claim 1, wherein said composition further comprises a support chosen from water and a mixture of water and at least one organic solvent.

17. The composition according to claim 1, wherein said composition has a pH from 2 to 11.

18. The composition according to claim 17, wherein said composition has a pH from 5 to 10.

19. The composition according to claim 1, wherein said composition further comprises at least one additional direct dye other than said at least one cationic direct dye.

20. The composition according to claim 19, wherein said at least one additional direct dye is chosen from nitrobenzene dyes, anthraquinone dyes, napthaquinone dyes, triarylmethane dyes, xanthene dyes and azo dyes.

21. The composition according to claim 1, wherein said composition further comprises at least one oxidation base chosen from para-phenylenediamines, bis(phenyl) alkylenediamines, para-aminophenols, ortho-aminophenols and heterocyclic bases.

22. The composition according to claim 21, wherein said at least one oxidation base is present in an amount ranging from 0.0005 to 12% by weight relative to the total weight of the dye composition.

23. The composition according to claim 22, wherein said at least one oxidation base is present in an amount ranging from 0.005 to 6% by weight relative to the total weight of the dye composition.

24. The composition according to claim 21, wherein said composition further comprises at least one coupler chosen from meta-phenylenediamines, meta-aminophenols, meta-diphenols and heterocyclic couplers.

25. The composition according to claim 24, wherein said at least one coupler is present in an amount ranging from 0.0001 to 10% by weight relative to the total weight of the dye composition.

26. The composition according to claim 25, wherein said at least one coupler represents from 0.005 to 5% by weight relative to the total weight of the dye composition.

27. The composition according to claim 21, wherein said composition further comprises at least one oxidizing agent.

28. The composition according to claim 27, wherein said at least one oxidizing agent is chosen from hydrogen peroxide, urea peroxide, alkali metal bromates, persalts and enzymes.

29. The composition according to claim 28, wherein said persalts are chosen from perborates and persulphates.

30. The composition according to claim 28, wherein said enzymes are chosen from peroxidases, lactases, and two-electron oxidoreductases.

31. A process for dyeing keratin fibers, comprising separately storing a first composition, separately storing a second composition, thereafter mixing said first and second compositions, applying said mixture to said fibers, and developing for a period of time sufficient to achieve a desired coloration, wherein said first composition comprises at least one cationic direct dye:

(i) wherein said at least one cationic dye is chosen from compounds of formula (I) below:

$$A\!-\!N\!=\!N\!-\!B \qquad (I)$$

in which:

the symbol A represents a group chosen from the structures $A_1$ to $A_3$ below:

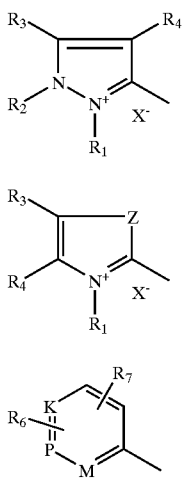

$A_1$ $A_2$ $A_3$ in which structures $A_1$ to $A_3$, $R_1$ is chosen from $C_1$–$C_4$ alkyl radicals, a phenyl radical which can be substituted with a $C_1$–$C_4$ alkyl radical or a halogen atom chosen from chlorine, bromine, iodine and fluorine;

$R_2$ is chosen from $C_1$–$C_4$ alkyl radicals and a phenyl radical;

$R_3$ and $R_4$, which may be identical or different, are chosen from $C_1$–$C_4$ alkyl radicals, a phenyl radical or, together form, in $A_1$, a benzene ring substituted with at least one radical chosen from $C_1$–$C_4$ alkyl radicals, $C_1$–$C_4$ alkoxy radicals and $NO_2$ radicals or, together form, in $A_2$, a benzene ring optionally substituted with at least one radical chosen from $C_1$–$C_4$ alkyl radicals, $C_1$–$C_4$ alkoxy radicals and $NO_2$ radicals;

$R_3$ can be further chosen from a hydrogen atom;

Z is chosen from an oxygen atom, a sulphur atom and —$NR_2$ radicals;

M is chosen from a —CH radical, —$C(C_1$–$C_4$ alkyl) radicals and —$N^+R_5(X^-)_r$ radicals;

K is chosen from a —CH radical, —$C(C_1$–$C_4$ alkyl) radicals and —$N^+R_5(X^-)_r$ radicals;

P is chosen from a —CH radical, —$C(C_1$–$C_4$ alkyl) radicals and —$N^+R_5(X^-)_r$ radicals;

wherein r denotes zero or 1;

wherein $R_5$ is chosen from an $O^-$ anion, $C_1$–$C_4$ alkoxy radicals and $C_1$–$C_4$ alkyl radicals;

$R_6$ and $R_7$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals, and —$NO_2$ radicals;

$X^-$ is chosen from anions;

with the proviso that, wherein if $R_4$ is a $C_1$–$C_4$ alkyl radical and Z denotes a sulphur atom, $R_3$ is not a hydrogen atom;

wherein if $R_5$ is $O^-$, then r is zero;

wherein if K or P or M is —$N^+$—($C_1$–$C_4$ alkyl)$X^-$, either $R_6$ or $R_7$ is not a hydrogen atom;

wherein if K is —$N^+R_5(X^-)_r$, M and P are the same and are chosen from a —CH radical and —$C(C_1$–$C_4$ alkyl) radicals;

wherein if M is —$N^+R_5(X^-)_r$, K and P are the same and are chosen from a —CH radical and —$C(C_1$–$C_4$ alkyl) radicals;

if P denotes —$N^+R_5(X^-)_r$, K and M are the same and are chosen from a —CH radical and —$C(C_1$–$C_4$ alkyl) radicals;

if Z is —$NR_2$ with $R_2$ being a radical chosen from $C_1$–$C_4$ alkyl radicals, at least one of the radicals $R_1$, $R_3$ or $R_4$ of $A_2$ is not chosen from $C_1$–$C_4$ alkyl radicals;

the symbol B is chosen from:

(a) a group of structure $B_1$ below:

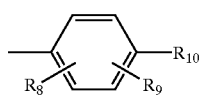

$B_1$ in which structure $B_1$, $R_8$ is chosen from a hydrogen atom, a halogen atom chosen from chlorine, bromine, iodine and fluorine, $C_1$–$C_4$ alkyl radicals, $C_1$–$C_4$ alkoxy radicals, a radical —OH, a radical —$NO_2$, —$NHR_{11}$ radicals, —$NR_{12}R_{13}$ radicals, —NHCO ($C_1$–$C_4$) alkyl radicals, or forms with $R_9$ a 5- or 6-membered ring which may or may not contain at least one hetero atom chosen from nitrogen, oxygen and sulphur;

$R_9$ is chosen from a hydrogen atom, a halogen atom chosen from chlorine, bromine, iodine and fluorine, $C_1$–$C_4$ alkyl radicals, $C_1$–$C_4$ alkoxy radicals, or forms, with $R_{10}$ or $R_{11}$, a 5- or 6-membered ring which may or may not contain at least one hetero atom chosen from nitrogen, oxygen and sulphur;

$R_{10}$ is chosen from a hydrogen atom, an —OH radical, —$NHR_{11}$ radicals and —$NR_{12}R_{13}$ radicals;

$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;

$R_{12}$ and $R_{13}$, which may be identical or different, is chosen from $C_1$–$C_4$ alkyl radicals, $C_1$–$C_4$ monohydroxyalkyl radicals and $C_2$–$C_4$ polyhydroxyalkyl radicals;

(b) 5- and 6-membered nitrogenous heterocyclic groups optionally containing other heteroatoms or carbonyl groups and optionally substituted with at least one radical chosen from $C_1$–$C_4$ alkyl radicals, an amino radical, a phenyl radical, and wherein said second composition comprises at least one oxidizing agent and at least one thickening polymer, wherein said at least one thickening polymer is chosen from polymers comprising:

(ii)$_2$—biopolysaccharide gums of microbial origin, except for xanthan gum;

(ii)$_3$—gums derived from plant exudates;

(ii)$_4$—pectins;

(ii)$_5$—alginates;

(ii)$_6$—starches; and (ii)$_7$—carboxyalkylcelluloses.

32. A multi-compartment dyeing kit, comprising at least two separate compartments, wherein a first compartment contains a first composition and a second compartment contains a second composition, wherein said first composition comprises at least one cationic direct dye, at least one thickening polymer and at least one oxidation base, (i) wherein said at least one cationic dye is chosen from compounds of formula (I) below:

$$A\text{=}N\text{=}N\text{—}B \qquad (I)$$

in which:
the symbol A represents a group chosen from the structures $A_1$ to $A_3$ below:

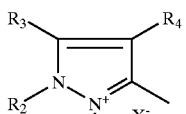

$A_1$

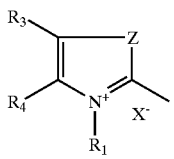

$A_2$

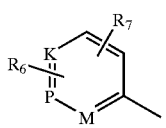

$A_3$ in which structures $A_1$ to $A_3$,
$R_1$ is chosen from $C_1-C_4$ alkyl radicals, a phenyl radical which can be substituted with a $C_1-C_4$ alkyl radical or a halogen atom chosen from chlorine, bromine, iodine and fluorine;
$R_2$ is chosen from $C_1-C_4$ alkyl radicals and a phenyl radical;
$R_3$ and $R_4$, which may be identical or different, are chosen from $C_1-C_4$ alkyl radicals, a phenyl radical or,
together form, in $A_1$, a benzene ring substituted with at least one radical chosen from $C_1-C_4$ alkyl radicals, $C_1-C_4$ alkoxy radicals and $NO_2$ radicals or,
together form, in $A_2$, a benzene ring optionally substituted with at least one radical chosen from $C_1-C_4$ alkyl radicals, $C_1-C_4$ alkoxy radicals and $NO_2$ radicals;
$R_3$ can be further chosen from a hydrogen atom;
Z is chosen from an oxygen atom, a sulphur atom and —$NR_2$ radicals;
M is chosen from a —CH radical, —$C(C_1-C_4$ alkyl) radicals and —$N^+R_5(X^-)_r$ radicals;
K is chosen from a —CH radical, —$C(C_1-C_4$ alkyl) radicals and —$N^+R_5(X^-)_r$ radicals;
P is chosen from a —CH radical, —$C(C_1-C_4$ alkyl) radicals and —$N^+R_5(X^-)_r$ radicals;
wherein r denotes zero or 1;
wherein $R_5$ is chosen from an $O^-$ anion, $C_1-C_4$ alkoxy radicals and $C_1-C_4$ alkyl radicals;
$R_6$ and $R_7$, which may be identical or different, are chosen from a hydrogen atom, halogen atoms chosen from chlorine, bromine, iodine and fluorine, $C_1-C_4$ alkyl radicals, $C_1-C_4$ alkoxy radicals, and —$NO_2$ radicals;
$X^-$ is chosen from anions;
with the proviso that,
wherein if $R_4$ is a $C_1-C_4$ alkyl radical and Z denotes a sulphur atom, $R_3$ is not a hydrogen atom;
wherein if $R_5$ is $O^-$, then r is zero;
wherein if K or P or M is —$N^+$—$(C_1-C_4$ alkyl)$X^-$, either $R_6$ or $R_7$ is not a hydrogen atom;
wherein if K is —$N^+R_5(X^-)_r$, M and P are the same and are chosen from a —CH radical and —$C(C_1-C_4$ alkyl) radicals;

wherein if M is —$N^+R_5(X^-)_r$, K and P are the same and are chosen from a —CH radical and —$C(C_1-C_4$ alkyl) radicals;
if P denotes —$N^+R_5(X^-)_r$, K and M are the same and are chosen from a —CH radical and —$C(C_1-C_4$ alkyl) radicals;
if Z is —$NR_2$ with $R_2$ being a radical chosen from $C_1-C_4$ alkyl radicals, at least one of the radicals $R_1$, $R_3$ or $R_4$ of $A_2$ is not chosen from $C_1-C_4$ alkyl radicals;
the symbol B is chosen from:
(a) a group of structure $B_1$ below:

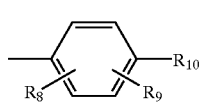

$B_1$ in which structure $B_1$,
$R_8$ is chosen from a hydrogen atom, a halogen atom chosen from chlorine, bromine, iodine and fluorine, $C_1-C_4$ alkyl radicals, $C_1-C_4$ alkoxy radicals, a radical —OH, a radical —$NO_2$, —$NHR_{11}$ radicals, —$NR_{12}R_{13}$ radicals, —NHCO $(C_1-C_4)$ alkyl radicals, or forms with $R_9$ a 5- or 6-membered ring which may or may not contain at least one hetero atom chosen from nitrogen, oxygen and sulphur;
$R_9$ is chosen from a hydrogen atom, a halogen atom chosen from chlorine, bromine, iodine and fluorine, $C_1-C_4$ alkyl radicals, $C_1-C_4$ alkoxy radicals, or forms, with $R_{10}$ or $R_{11}$, a 5- or 6-membered ring which may or may not contain at least one hetero atom chosen from nitrogen, oxygen and sulphur;
$R_{10}$ is chosen from a hydrogen atom, an —OH radical, —$NHR_{11}$ radicals and —$NR_{12}R_{13}$ radicals;
$R_{11}$ is chosen from a hydrogen atom, $C_1-C_4$ alkyl radicals, $C_1-C_4$ monohydroxyalkyl radicals, $C_2-C_4$ polyhydroxyalkyl radicals and a phenyl radical;
$R_{12}$ and $R_{13}$, which may be identical or different, is chosen from $C_1-C_4$ alkyl radicals, $C_1-C_4$ monohydroxyalkyl radicals and $C_2-C_4$ polyhydroxyalkyl radicals;
(b) 5- and 6-membered nitrogenous heterocyclic groups optionally containing other heteroatoms or carbonyl groups and optionally substituted with at least one radical chosen from $C_1-C_4$ alkyl radicals, an amino radical, a phenyl radical, and
wherein said at least one thickening polymer is chosen from polymers comprising:
(ii)$_2$—biopolysaccharide gums of microbial origin;
(ii)$_3$—gums derived from plant exudates;
(ii)$_4$—pectins;
(ii)$_5$—alginates;
(ii)$_6$—starches; and
(ii)$_7$—carboxyalkylcelluloses;
and wherein said second composition comprises at least one oxidizing agent.

33. A multi-compartment dyeing kit, comprising at least two separate compartments, wherein a first compartment contains a first composition and a second compartment contains a second composition,
wherein said first composition comprises at least one oxidation base and at least one cationic direct dye:
(i) wherein said at least one cationic dye is chosen from compounds of formula (I) below.

$$A-N=N-B \qquad (I)$$

in which:
the symbol A represents a group chosen from the structures $A_1$ to $A_3$ below:

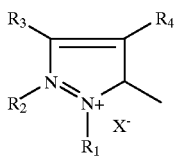

$A_1$

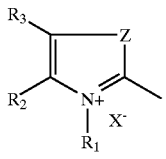

$A_2$

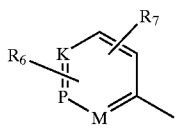

$A_3$ in which structures $A_1$ to $A_3$,
$R_1$ is chosen from $C_1$–$C_4$ alkyl radicals, a phenyl radical which can be substituted with a $C_1$–$C_4$ alkyl radical or a halogen atom chosen from chlorine, bromine, iodine and fluorine;
$R_2$ is chosen from $C_1$–$C_4$ alkyl radicals and a phenyl radical;
$R_3$ and $R_4$, which may be identical or different, are chosen from $C_1$–$C_4$ alkyl radicals, a phenyl radical or,
together form, in $A_1$, a benzene ring substituted with at least one radical chosen from $C_1$–$C_4$ alkyl radicals, $C_1$–$C_4$ alkoxy radicals and $NO_2$ radicals or,
together form, in $A_2$, a benzene ring optionally substituted with at least one radical chosen from $C_1$–$C_4$ alkyl radicals, $C_1$–$C_4$ alkoxy radicals and $NO_2$ radicals;
$R_3$ can be further chosen from a hydrogen atom;
Z is chosen from an oxygen atom, a sulphur atom and —$NR_2$ radicals;
M is chosen from a —CH radical, —C($C_1$–$C_4$ alkyl) radicals and —$N^+R_5(X^-)_r$ radicals;
K is chosen from a —CH radical, —C($C_1$–$C_4$ alkyl) radicals and —$N^+R_5(X^-)_r$ radicals;
P is chosen from a —CH radical, —C($C_1$–$C_4$ alkyl) radicals and —$N^+R_5(X^-)_r$ radicals;
wherein r denotes zero or 1;
wherein $R_5$ is chosen from an $O^-$ anion, $C_1$–$C_4$ alkoxy radicals and $C_1$–$C_4$ alkyl radicals;
$R_6$ and $R_7$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals, and —$NO_2$ radicals;
$X^-$ is chosen from anions;
with the proviso that,
wherein if $R_4$ is a $C_1$–$C_4$ alkyl radical and Z denotes a sulphur atom, $R_3$ is not a hydrogen atom;
wherein if $R_5$ is $O^-$, then r is zero;
wherein if K or P or M is —$N^+$—($C_1$–$C_4$ alkyl)$X^-$, either $R_6$ or $R_7$ is not a hydrogen atom;
wherein if K is —$N^+R_5(X^-)_r$, M and P are the same and are chosen from a —CH radical and —C($C_1$–$C_4$ alkyl) radicals;

wherein if M is —$N^+R_5(X^-)_r$, K and P are the same and are chosen from a —CH radical and —C($C_1$–$C_4$ alkyl) radicals;
if P denotes —$N^+R_5(X^-)_r$, K and M are the same and are chosen from a —CH radical and —C($C_1$–$C_4$ alkyl) radicals;
if Z is —$NR_2$ with $R_2$ being a radical chosen from $C_1$–$C_4$ alkyl radicals, at least one of the radicals $R_1$, $R_3$ or $R_4$ of $A_2$ is not chosen from $C_1$–$C_4$ alkyl radicals;
the symbol B is chosen from:
(a) a group of structure $B_1$ below:

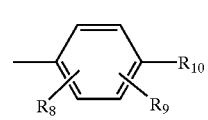

$B_1$ in which structure $B_1$,
$R_8$ is chosen from a hydrogen atom, a halogen atom chosen from chlorine, bromine, iodine and fluorine, $C_1$–$C_4$ alkyl radicals, $C_1$–$C_4$ alkoxy radicals, a radical —OH, a radical —$NO_2$, —$NHR_{11}$ radicals, —$NR_{12}R_{13}$ radicals, —$NHCO(C_1$–$C_4)$ alkyl radicals, or forms with $R_9$ a 5- or 6-membered ring which may or may not contain at least one hetero atom chosen from nitrogen, oxygen and sulphur;
$R_9$ is chosen from a hydrogen atom, a halogen atom chosen from chlorine, bromine, iodine and fluorine, $C_1$–$C_4$ alkyl radicals, $C_1$–$C_4$ alkoxy radicals, or forms, with $R_{10}$ or $R_{11}$, a 5- or 6-membered ring which may or may not contain at least one hetero atom chosen from nitrogen, oxygen and sulphur;
$R_{10}$ is chosen from a hydrogen atom, an —OH radical, —$NHR_{11}$ radicals and —$NR_{12}R_{13}$ radicals;
$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;
$R_{12}$ and $R_{13}$, which may be identical or different, is chosen from $C_1$–$C_4$ alkyl radicals, $C_1$–$C_4$ monohydroxyalkyl radicals and $C_2$–$C_4$ polyhydroxyalkyl radicals;
(b) 5- and 6-membered nitrogenous heterocyclic groups optionally containing other heteroatoms or carbonyl groups and optionally substituted with at least one radical chosen from $C_1$–$C_4$ alkyl radicals, an amino radical, a phenyl radical,
and wherein said second composition comprises at least one oxidizing agent and at least one thickening polymer,
wherein said at least one thickening polymer is chosen from polymers comprising:
(ii)$_2$—biopolysaccharide gums of microbial origin;
(ii)$_3$—gums derived from plant exudates;
(ii)$_4$—pectins;
(ii)$_5$—alginates;
(ii)$_6$—starches; and
(ii)$_7$—carboxyalkylcelluloses.
34. A multi-compartment dyeing kit, comprising at least two separate compartments, wherein a first compartment contains a first composition and a second compartment contains a second composition,
wherein said first composition comprises at least one thickening polymer and at least one cationic direct dye:
(i) wherein said at least one cationic dye is chosen from compounds of formula (I) below:

$$A—N=N—B \qquad (I)$$

in which:
   the symbol A represents a group chosen from the structures $A_1$ to $A_3$ below:

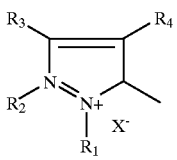

$A_1$

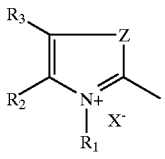

$A_2$

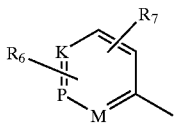

$A_3$ in which structures $A_1$ to $A_3$,
   $R_1$ is chosen from $C_1$–$C_4$ alkyl radicals, a phenyl radical which can be substituted with a $C_1$–$C_4$ alkyl radical or a halogen atom chosen from chlorine, bromine, iodine and fluorine;
   $R_2$ is chosen from $C_1$–$C_4$ alkyl radicals and a phenyl radical;
   $R_3$ and $R_4$, which may be identical or different, are chosen from $C_1$–$C_4$ alkyl radicals, a phenyl radical or,
      together form, in $A_1$, a benzene ring substituted with at least one radical chosen from $C_1$–$C_4$ alkyl radicals, $C_1$–$C_4$ alkoxy radicals and $NO_2$ radicals or,
      together form, in $A_2$, a benzene ring optionally substituted with at least one radical chosen from $C_1$–$C_4$ alkyl radicals, $C_1$–$C_4$ alkoxy radicals and $NO_2$ radicals;
   $R_3$ can be further chosen from a hydrogen atom;
   Z is chosen from an oxygen atom, a sulphur atom and —$NR_2$ radicals;
   M is chosen from a —CH radical, —$C(C_1$–$C_4$ alkyl) radicals and —$N^+R_5(X^-)_r$ radicals;
   K is chosen from a —CH radical, —$C(C_1$–$C_4$ alkyl) radicals and —$N^+R_5(X^-)_r$ radicals;
   P is chosen from a —CH radical, —$C(C_1$–$C_4$ alkyl) radicals and —$N^+R_5(X^-)_r$ radicals;
      wherein r denotes zero or 1;
      wherein $R_5$ is chosen from an $O^-$ anion, $C_1$–$C_4$ alkoxy radicals and $C_1$–$C_4$ alkyl radicals;
   $R_6$ and $R_7$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals, and —$NO_2$ radicals;
   $X^-$ is chosen from anions;
   with the proviso that,
   wherein if $R_4$ is a $C_1$–$C_4$ alkyl radical and Z denotes a sulphur atom, $R_3$ is not a hydrogen atom;
   wherein if $R_5$ is $O^-$, then r is zero;
   wherein if K or P or M is —$N^+$—$(C_1$–$C_4$ alkyl)$X^-$, either $R_6$ or $R_7$ is not a hydrogen atom;
   wherein if K is —$N^+R_5(X^-)_r$, M and P are the same and are chosen from a —CH radical and —$C(C_1$–$C_4$ alkyl) radicals;

wherein if M is —$N^+R_5(X^-)_r$, K and P are the same and are chosen from a —CH radical and —$C(C_1$–$C_4$ alkyl) radicals;
   if P denotes —$N^+R_5(X^-)_r$, K and M are the same and are chosen from a —CH radical and —$C(C_1$–$C_4$ alkyl) radicals;
   if Z is —$NR_2$ with $R_2$ bag a radical chosen from $C_1$–$C_4$ alkyl radicals, at least one of the radicals $R_1$, $R_3$ or $R_4$ of $A_2$ is not chosen from $C_1$–$C_4$ alkyl radicals;
   the symbol B is chosen from:
   (a) a group of structure $B_1$ below:

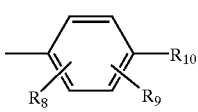

$B_1$ in which structure $B_1$,
   $R_8$ is chosen from a hydrogen atom, a halogen atom chosen from chlorine, bromine, iodine and fluorine, $C_1$–$C_4$ alkyl radicals, $C_1$–$C_4$ alkoxy radicals, a radical —OH, a radical —$NO_2$, —$NHR_{11}$ radicals, —$NR_{12}R_{13}$ radicals, —NHCO ($C_1$–$C_4$) alkyl radicals, or forms with $R_9$ a 5- or 6-membered ring which may or may not contain at least one hetero atom chosen from nitrogen, oxygen and sulphur;
   $R_9$ is chosen from a hydrogen atom, a halogen atom chosen from chlorine, bromine, iodine and fluorine, $C_1$–$C_4$ alkyl radicals, $C_1$–$C_4$ alkoxy radicals, or forms, with $R_{10}$ or $R_{11}$, a 5- or 6-membered ring which may or may not contain at least one hetero atom chosen from nitrogen, oxygen and sulphur;
   $R_{10}$ is chosen from a hydrogen atom, an —OH radical, —$NHR_{11}$ radicals and —$NR_{12}R_{13}$ radicals;
   $R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;
   $R_{12}$ and $R_{13}$, which may be identical or different, is chosen from $C_1$–$C_4$ alkyl radicals, $C_1$–$C_4$ monohydroxyalkyl radicals and $C_2$–$C_4$ polyhydroxyalkyl radicals;
   (b) 5- and 6-membered nitrogenous heterocyclic groups optionally containing other heteroatoms or carbonyl groups and optionally substituted with at least one radical chosen from $C_1$–$C_4$ alkyl radicals, an amino radical, a phenyl radical, and
   wherein said at least one thickening polymer is chosen from polymers comprising:
      (ii)$_2$—biopolysaccharide gums of microbial origin, except for xanthan gum;
      (ii)$_3$—gums derived from plant exudates;
      (ii)$_4$—pectins;
      (ii)$_5$—alginates;
      (ii)$_6$—starches; and
      (ii)$_7$—carboxyalkylcelluloses;
   and wherein said second composition comprises at least one oxidizing agent.

35. A multi-compartment dyeing kit, comprising at least two separate compartments, wherein a first compartment contains a first composition and a second compartment contains a second composition,
   wherein said first composition comprises at least one cationic direct dye:
   (i) wherein said at least one cationic dye is chosen from compounds of formula (I) below:

(I)

in which:
the symbol A represents a group chosen from the structures $A_1$ to $A_3$ below:

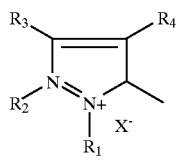

$A_1$

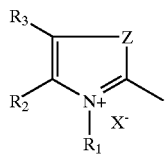

$A_2$

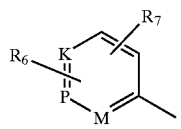

$A_3$ in which structures $A_1$ to $A_3$,
$R_1$ is chosen from $C_1-C_4$ alkyl radicals, a phenyl radical which can be substituted with a $C_1-C_4$ alkyl radical or a halogen atom chosen from chlorine, bromine, iodine and fluorine;
$R_2$ is chosen from $C_1-C_4$ alkyl radicals and a phenyl radical;
$R_3$ and $R_4$, which may be identical or different, are chosen from $C_1-C_4$ alkyl radicals, a phenyl radical or,
together form, in $A_1$, a benzene ring substituted with at least one radical chosen from $C_1-C_4$ alkyl radicals, $C_1-C_4$ alkoxy radicals and $NO_2$ radicals or,
together form, in $A_2$, a benzene ring optionally substituted with at least one radical chosen from $C_1-C_4$ alkyl radicals, $C_1-C_4$ alkoxy radicals and $NO_2$ radicals;
$R_3$ can be further chosen from a hydrogen atom;
Z is chosen from an oxygen atom, a sulphur atom and $-NR_2$ radicals;
M is chosen from a $-CH$ radical, $-C(C_1-C_4$ alkyl) radicals and $-N^+R_5(X^-)_r$ radicals;
K is chosen from a $-CH$ radical, $-C(C_1-C_4$ alkyl) radicals and $-N^+R_5(X^-)_r$ radicals;
P is chosen from a $-CH$ radical, $-C(C_1-C_4$ alkyl) radicals and $-N^+R_5(X^-)_r$ radicals;
wherein r denotes zero or 1;
wherein $R_5$ is chosen from an $O^-$ anion, $C_1-C_4$ alkoxy radicals and $C_1-C_4$ alkyl radicals;
$R_6$ and $R_7$, which may be identical or different, are chosen from a hydrogen atom, halogen atoms chosen from chlorine, bromine, iodine and fluorine, $C_1-C_4$ alkyl radicals, $C_1-C_4$ alkoxy radicals, and $-NO_2$ radicals;
$X^-$ is chosen from anions;
with the proviso that,
wherein if $R_4$ is a $C_1-C_4$ alkyl radical and Z denotes a sulphur atom, $R_3$ is not a hydrogen atom;
wherein if $R_5$ is $O^-$, then r is zero;
wherein if K or P or M is $-N^+-(C_1-C_4$ alkyl)$X^-$, either $R_6$ or $R_7$ is not a hydrogen atom;
wherein if K is $N^+R_5(X^-)_r$, M and P are the same and are chosen from a $-CH$ radical and $-C(C_1-C_4$ alkyl) radicals;

wherein if M is $-N^+R_5(X^-)_r$, K and P are the same and are chosen from a $-CH$ radical and $-C(C_1-C_4$ alkyl) radicals;
if P denotes $-N^+R_5(X^-)_r$, K and M are the same and are chosen from a $-CH$ radical and $-C(C_1-C_4$ alkyl) radicals;
if Z is $-NR_2$ with $R_2$ being a radical chosen from $C_1-C_4$ alkyl radicals, at least one of the radicals $R_1$, $R_3$ or $R_4$ of $A_2$ is not chosen from $C_1-C_4$ alkyl radicals;
the symbol B is chosen from:
(a) a group of structure $B_1$ below:

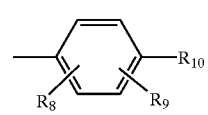

$B_1$ in which structure $B_1$,
$R_8$ is chosen from a hydrogen atom, a halogen atom chosen from chlorine, bromine, iodine and fluorine, $C_1-C_4$ alkyl radicals, $C_1-C_4$ alkoxy radicals, a radical $-OH$, a radical $-NO_2$, $-NHR_{11}$ radicals, $-NR_{12}R_{13}$ radicals, $-NHCO$ ($C_1-C_4$) alkyl radicals, or forms with $R_9$ a 5- or 6-membered ring which may or may not contain at least one hetero atom chosen from nitrogen, oxygen and sulphur;
$R_9$ is chosen from a hydrogen atom, a halogen atom chosen from chlorine, bromine, iodine and fluorine, $C_1-C_4$ alkyl radicals, $C_1-C_4$ alkoxy radicals, or forms, with $R_{10}$ or $R_{11}$, a 5- or 6-membered ring which may or may not contain at least one hetero atom chosen from nitrogen, oxygen and sulphur;
$R_{10}$ is chosen from a hydrogen atom, an $-OH$ radical, $-NHR_{11}$ radicals and $-NR_{12}R_{13}$ radicals;
$R_{11}$ is chosen from a hydrogen atom, $C_1-C_4$ alkyl radicals, $C_1-C_4$ monohydroxyalkyl radicals, $C_2-C_4$ polyhydroxyalkyl radicals and a phenyl radical;
$R_{12}$ and $R_{13}$, which may be identical or different, is chosen from $C_1-C_4$ alkyl radicals, $C_1-C_4$ monohydroxyalkyl radicals and $C_2-C_4$ polyhydroxyalkyl radicals;
(b) 5- and 6-membered nitrogenous heterocyclic groups optionally containing other heteroatoms or carbonyl groups and optionally substituted with at least one radical chosen from $C_1-C_4$ alkyl radicals, an amino radical, a phenyl radical,
and wherein said second composition comprises at least one oxidizing agent and at least one thickening polymer,
wherein said at least one thickening polymer is chosen from polymers comprising:
(ii)$_2$—biopolysaccharide gums of microbial origin, except for xanthan gum;
(ii)$_3$—gums derived from plant exudates;
(ii)$_4$—pectins;
(ii)$_5$—alginates;
(ii)$_6$—starches; and
(ii)$_7$—carboxyalkylcelluloses.

36. A process for dyeing keratin fibers, comprising applying a composition for the dyeing of keratin fibers to said keratin fibers and developing for a period of time sufficient to achieve a desired coloration, wherein said composition comprises:
i) at least one cationic dye chosen from compounds of formula (I) below:

(I)

in which:

the symbol A represents a group chosen from the structures $A_1$ to $A_3$ below:

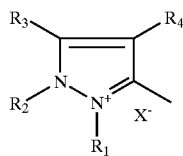 $A_1$

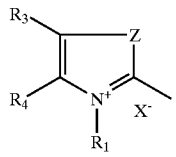 $A_2$

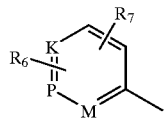 $A_3$ in which structures $A_1$ to $A_3$, $R_1$ is chosen from $C_1$–$C_4$ alkyl radicals, a phenyl radical which can be substituted with a $C_1$–$C_4$ alkyl radical or a halogen atom chosen from chlorine, bromine, iodine and fluorine;

$R_2$ is chosen from $C_1$–$C_4$ alkyl radicals and a phenyl radical;

$R_3$ and $R_4$, which may be identical or different, are chosen from $C_1$–$C_4$ alkyl radicals, a phenyl radical or, together form, in $A_1$, a benzene ring substituted with at least one radical chosen from $C_1$–$C_4$ alkyl radicals, $C_1$–$C_4$ alkoxy radicals and $NO_2$ radicals or, together form, in $A_2$, a benzene ring optionally substituted with at least one radical chosen from $C_1$–$C_4$ alkyl radicals, $C_1$–$C_4$ alkoxy radicals and $NO_2$ radicals;

$R_3$ can be further chosen from a hydrogen atom;

Z is chosen from an oxygen atom, a sulphur atom and —$NR_2$ radicals;

M is chosen from a —CH radical, —C($C_1$–$C_4$ alkyl) radicals and —$N^+R_5(X^-)_r$ radicals;

K is chosen from a —CH radical, —C($C_1$–$C_4$ alkyl) radicals and —$N^+R_5(X^-)_r$ radicals;

P is chosen from a —CH radical, —C($C_1$–$C_4$ alkyl) radicals and —$N^+R_5(X^-)_r$ radicals;

wherein r denotes zero or 1;

wherein $R_5$ is chosen from an $O^-$ anion, $C_1$–$C_4$ alkoxy radicals and $C_1$–$C_4$ alkyl radicals;

$R_6$ and $R_7$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals, and —$NO_2$ radicals;

$X^-$ is chosen from anions;

with the proviso that, wherein if $R_4$ is a $C_1$–$C_4$ alkyl radical and Z denotes a sulphur atom, $R_3$ is not a hydrogen atom;

wherein if $R_5$ is $O^-$, then r is zero;

wherein if K or P or M is —$N^+$—($C_1$–$C_4$ alkyl)$X^-$, either $R_6$ or $R_7$ is not a hydrogen atom;

wherein if K is —$N^+R_5(X^-)_r$, M and P are the same and are chosen from a —CH radical and —C($C_1$–$C_4$ alkyl) radicals;

wherein if M is —$N^+R_5(X^-)_r$, K and P are the same and are chosen from a —CH radical and —C($C_1$–$C_4$ alkyl) radicals;

if P denotes —$N^+R_5(X^-)_r$, K and M are the same and are chosen from a —CH radical and —C($C_1$–$C_4$ alkyl) radicals;

if Z is —$NR_2$ with $R_2$ being a radical chosen from $C_1$–$C_4$ alkyl radicals, at least one of the radicals $R_1$, $R_3$ or $R_4$ of $A_2$ is not chosen from $C_1$–$C_4$ alkyl radicals;

the symbol B is chosen from:

(a) a group of structure $B_1$ below:

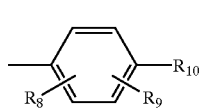 $B_1$ in which structure $B_1$, $R_8$ is chosen from a hydrogen atom, a halogen atom chosen from chlorine, bromine, iodine and fluorine, $C_1$–$C_4$ alkyl radicals, $C_1$–$C_4$ alkoxy radicals, a radical —OH, a radical —$NO_2$, —$NHR_{11}$ radicals, —$NR_{12}R_{13}$ radicals, —NHCO ($C_1$–$C_4$) alkyl radicals, or forms with $R_9$ a 5- or 6-membered ring which may or may not contain at least one hetero atom chosen from nitrogen, oxygen and sulphur;

$R_9$ is chosen from a hydrogen atom, a halogen atom chosen from chlorine, bromine, iodine and fluorine, $C_1$–$C_4$ alkyl radicals, $C_1$–$C_4$ alkoxy radicals, or forms, with $R_{10}$ or $R_{11}$, a 5- or 6-membered ring which may or may not contain at least one hetero atom chosen from nitrogen, oxygen and sulphur;

$R_{10}$ is chosen from a hydrogen atom, an —OH radical, —$NHR_{11}$ radicals and —$NR_{12}R_{13}$ radicals;

$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;

$R_{12}$ and $R_{13}$, which may be identical or different, is chosen from $C_1$–$C_4$ alkyl radicals, $C_1$–$C_4$ monohydroxyalkyl radicals and $C_2$–$C_4$ polyhydroxyalkyl radicals;

(b) 5- and 6-membered nitrogenous heterocyclic groups optionally containing other heteroatoms or carbonyl groups and optionally substituted with at least one radical chosen from $C_1$–$C_4$ alkyl radicals, an amino radical, a phenyl radical, and (ii) at least one thickening polymer chosen from polymers comprising:

(ii)$_2$—biopolysaccharide gums of microbial origin, except for xanthan gum;

(ii)$_3$—gums derived from plant exudates;

(ii)$_4$—pectins;

(ii)$_5$—alginates; and (ii)$_6$—starches.

37. The process according to claim 36, wherein said process further comprises rinsing said fibers, then drying said fibers.

38. The process according to claim 36, wherein said process further comprises washing said fibers with shampoo, a second rinsing of said fibers and drying of said fibers.

39. A process for dyeing keratin fibers, comprising
separately storing a first composition,
separately storing a second composition,
thereafter mixing said first and second compositions,
applying said mixture to said fibers, and
developing for a period of time sufficient to achieve a desired coloration,
wherein said first composition comprises at least one cationic direct dye, at least one thickening polymer, and at least one oxidation base:
i) wherein said at least one cationic dye is chosen from compounds of formula (I) below:

  (I)

in which:
the symbol A represents a group chosen from the structures $A_1$ to $A_3$ below:

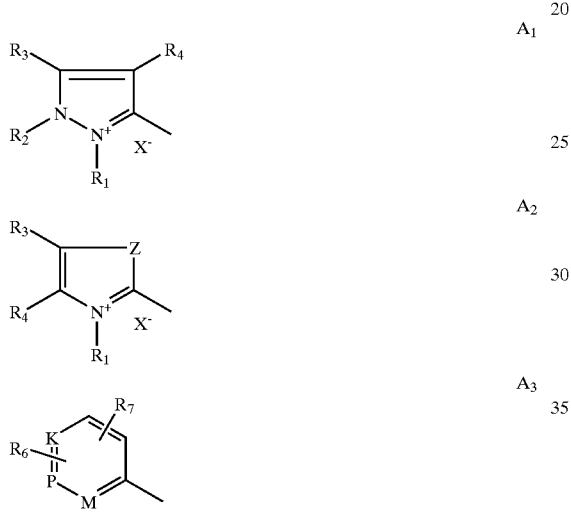

in which structures $A_1$ to $A_3$,
$R_1$ is chosen from $C_1$–$C_4$ alkyl radicals, a phenyl radical which can be substituted with a $C_1$–$C_4$ alkyl radical or a halogen atom chosen from chlorine, bromine, iodine and fluorine;
$R_2$ is chosen from $C_1$–$C_4$ alkyl radicals and a phenyl radical;
$R_3$ and $R_4$, which may be identical or different, are chosen from $C_1$–$C_4$ alkyl radicals, a phenyl radical or,
together form, in $A_1$, a benzene ring substituted with at least one radical chosen from $C_1$–$C_4$ alkyl radicals, $C_1$–$C_4$ alkoxy radicals and $NO_2$ radicals or,
together form, in $A_2$, a benzene ring optionally substituted with at least one radical chosen from $C_1$–$C_4$ alkyl radicals, $C_1$–$C_4$ alkoxy radicals and $NO_2$ radicals;
$R_3$ can be further chosen from a hydrogen atom;
Z is chosen from an oxygen atom, a sulphur atom and —$NR_2$ radicals;
M is chosen from a —CH radical, —C($C_1$–$C_4$ alkyl) radicals and —$N^+R_5(X^-)_r$ radicals;
K is chosen from a —CH radical, —C($C_1$–$C_4$ alkyl) radicals and —$N^+R_5(X^-)_r$ radicals;
P is chosen from a —CH radical, —C($C_1$–$C_4$ alkyl) radicals and —$N^+R_5(X^-)_r$ radicals;
wherein r denotes zero or 1;
wherein $R_5$ is chosen from an $O^-$ anion, $C_1$–$C_4$ alkoxy radicals and $C_1$–$C_4$ alkyl radicals;
$R_6$ and $R_7$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals, and —$NO_2$ radicals;
$X^-$ is chosen from anions;
with the proviso that,
wherein if $R_4$ is a $C_1$–$C_4$ alkyl radical and Z denotes a sulphur atom, $R_3$ is not a hydrogen atom;
wherein if $R_5$ is $O^-$, then r is zero;
wherein if K or P or M is —$N^+$—($C_1$–$C_4$ alkyl)$X^-$, either $R_6$ or $R_7$ is not a hydrogen atom;
wherein if K is —$N^+R_5(X^-)_r$, M and P are the same and are chosen from a —CH radical and —C($C_1$–$C_4$ alkyl) radicals;
wherein if M is —$N^+R_5(X^-)_r$, K and P are the same and are chosen from a —CH radical and —C($C_1$–$C_4$ alkyl) radicals;
if P denotes —$N^+R_5(X^-)_r$, K and M are the same and are chosen from a—CH radical and —C($C_1$–$C_4$ alkyl) radicals;
if Z is —$NR_2$ with $R_2$ being a radical chosen from $C_1$–$C_4$ alkyl radicals, at least one of the radicals $R_1$, $R_3$ or $R_4$ of $A_2$ is not chosen from $C_1$–$C_4$ alkyl radicals;
the symbol B is chosen from:
(a) a group of structure $B_1$ below:

in which structure $B_1$,
$R_8$ is chosen from a hydrogen atom, a halogen atom chosen from chlorine, bromine, iodine and fluorine, $C_1$–$C_4$ alkyl radicals, $C_1$–$C_4$ alkoxy radicals, a radical —OH, a radical —$NO_2$, —$NHR_{11}$ radicals, —$NR_{12}R_{13}$ radicals, —NHCO ($C_1$–$C_4$) alkyl radicals, or forms with $R_9$ a 5- or 6-membered ring which may or may not contain at least one hetero atom chosen from nitrogen, oxygen and sulphur;
$R_9$ is chosen from a hydrogen atom, a halogen atom chosen from chlorine, bromine, iodine and fluorine, $C_1$–$C_4$ alkyl radicals, $C_1$–$C_4$ alkoxy radicals, or forms, with $R_{10}$ or $R_{11}$, a 5- or 6-membered ring which may or may not contain at least one hetero atom chosen from nitrogen, oxygen and sulphur;
$R_{10}$ is chosen from a hydrogen atom, an —OH radical, —$NHR_{11}$ radicals and —$NR_{12}R_{13}$ radicals;
$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;
$R_{12}$ and $R_{13}$, which may be identical or different, is chosen from $C_1$–$C_4$ alkyl radicals, $C_1$–$C_4$ monohydroxyalkyl radicals and $C_2$–$C_4$ polyhydroxyalkyl radicals;
(b) 5- and 6-membered nitrogenous heterocyclic groups optionally containing other heteroatoms or carbonyl groups and optionally substituted with at least one radical chosen from $C_1$–$C_4$ alkyl radicals, an amino radical, a phenyl radical, and wherein said at least one thickening polymer chosen from polymers comprising:
(ii)$_2$—biopolysaccharide gums of microbial origin;
(ii)$_3$—gums derived from plant exudates;
(ii)$_4$—pectins;
(ii)$_5$—alginates;
(ii)$_6$—starches; and
(ii)$_7$—carboxyalkylcelluloses; and
wherein said second composition comprises at least one oxidizing agent.

40. A process for dyeing keratin fibers, comprising
separately storing a first composition,
separately storing a second composition,
thereafter mixing said first and second compositions,
applying said mixture to said fibers, and
developing for a period of time sufficient to achieve a desired coloration,
wherein said first composition comprises at least one oxidation base and at least one cationic direct dye:
i) wherein said at least one cationic dye is chosen from compounds of formula (I) below:

in which:
the symbol A represents a group chosen from the structures $A_1$ to $A_3$ below:

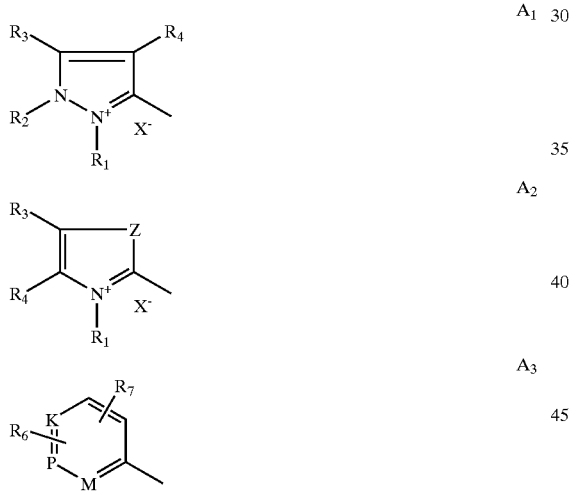

in which structures $A_1$ to $A_3$,
$R_1$ is chosen from $C_1$–$C_4$ alkyl radicals, a phenyl radical which can be substituted with a $C_1$–$C_4$ alkyl radical or a halogen atom chosen from chlorine, bromine, iodine and fluorine;
$R_2$ is chosen from $C_1$–$C_4$ alkyl radicals and a phenyl radical;
$R_3$ and $R_4$, which may be identical or different, are chosen from $C_1$–$C_4$ alkyl radicals, a phenyl radical or,
together form, in $A_1$, a benzene ring substituted with at least one radical chosen from $C_1$–$C_4$ alkyl radicals, $C_1$–$C_4$ alkoxy radicals and $NO_2$ radicals or,
together form, in $A_2$, a benzene ring optionally substituted with at least one radical chosen from $C_1$–$C_4$ alkyl radicals, $C_1$–$C_4$ alkoxy radicals and $NO_2$ radicals;

$R_3$ can be further chosen from a hydrogen atom;
Z is chosen from an oxygen atom, a sulphur atom and —$NR_2$ radicals;
M is chosen from a —CH radical, —C($C_1$–$C_4$ alkyl) radicals and —$N^+R_5(X^-)_r$ radicals;
K is chosen from a —CH radical, —C($C_1$–$C_4$ alkyl) radicals and —$N^+R_5(X^-)_r$ radicals;
P is chosen from a —CH radical, —C($C_1$–$C_4$ alkyl) radicals and —$N^+R_5(X^-)_r$ radicals;
wherein r denotes zero or 1;
wherein $R_5$ is chosen from an $O^-$ anion, $C_1$–$C_4$ alkoxy radicals and $C_1$–$C_4$ alkyl radicals;
$R_6$ and $R_7$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals, and —$NO_2$ radicals;
$X^-$ is chosen from anions;
with the proviso that,
wherein if $R_4$ is a $C_1$–$C_4$ alkyl radical and Z denotes a sulphur atom, $R_3$ is not a hydrogen atom;
wherein if $R_5$ is $O^-$, then r is zero;
wherein if K or P or M is —$N^+$—($C_1$–$C_4$ alkyl)$X^-$, either $R_6$ or $R_7$ is not a hydrogen atom;
wherein if K is —$N^+R_5(X^-)_r$, M and P are the same and are chosen from a —CH radical and —C($C_1$–$C_4$ alkyl) radicals;
wherein if M is —$N^+R_5(X^-)_r$, K and P are the same and are chosen from a —CH radical and —C($C_1$–$C_4$ alkyl) radicals;
if P denotes —$N^+R_5(X^-)_r$, K and M are the same and are chosen from a —CH radical and —C($C_1$–$C_4$ alkyl) radicals;
if Z is —$NR_2$ with $R_2$ being a radical chosen from $C_1$–$C_4$ alkyl radicals, at least one of the radicals $R_1$, $R_3$ or $R_4$ of $A_2$ is not chosen from $C_1$–$C_4$ alkyl radicals;
the symbol B is chosen from:
(a) a group of structure $B_1$ below:

in which structure $B_1$,
$R_8$ is chosen from a hydrogen atom, a halogen atom chosen from chlorine, bromine, iodine and fluorine, $C_1$–$C_4$ alkyl radicals, $C_1$–$C_4$ alkoxy radicals, a radical —OH, a radical —$NO_2$, —$NHR_{11}$ radicals, —$NR_{12}R_{13}$ radicals, —NHCO ($C_1$–$C_4$) alkyl radicals, or forms with $R_9$ a 5- or 6-membered ring which may or may not contain at least one hetero atom chosen from nitrogen, oxygen and sulphur;
$R_9$ is chosen from a hydrogen atom, a halogen atom chosen from chlorine, bromine, iodine and fluorine, $C_1$–$C_4$ alkyl radicals, $C_1$–$C_4$ alkoxy radicals, or forms, with $R_{10}$ or $R_{11}$, a 5- or 6-membered ring which may or may not contain at least one hetero atom chosen from nitrogen, oxygen and sulphur;
$R_{10}$ is chosen from a hydrogen atom, an —OH radical, —$NHR_{11}$ radicals and —$NR_{12}R_{13}$ radicals;
$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;
$R_{12}$ and $R_{13}$, which may be identical or different, is chosen from $C_1$–$C_4$ alkyl radicals, $C_1$–$C_4$ monohydroxyalkyl radicals and $C_2$–$C_4$ polyhydroxyalkyl radicals;

(b) 5- and 6-membered nitrogenous heterocyclic groups optionally containing other heteroatoms or carbonyl groups and optionally substituted with at least one radical chosen from $C_1$–$C_4$ alkyl radicals, an amino radical, a phenyl radical, and wherein said second composition comprises at least one oxidizing agent and at least one thickening polymer, wherein said at least one thickening polymer chosen from polymers comprising:
(ii)$_2$—biopolysaccharide gums of microbial origin;
(ii)$_3$—gums derived from plant exudates;
(ii)$_4$—pectins;
(ii)$_5$—alginates;
(ii)$_6$—starches; and
(ii)$_7$—carboxyalkylcelluloses.

41. A process for dyeing keratin fibers, comprising
separately storing a first composition,
separately storing a second composition,
thereafter mixing said first and second compositions,
applying said mixture to said fibers, and
developing for a period of time sufficient to achieve a desired coloration,
wherein said first composition comprises at least one cationic direct dye and at least one thickening polymer:
(i) wherein said at least one cationic dye is chosen from compounds of formula (I) below:

$$A\text{—}N\text{=}N\text{—}B \qquad (I)$$

in which:
the symbol A represents a group chosen from the structures $A_1$ to $A_3$ below:

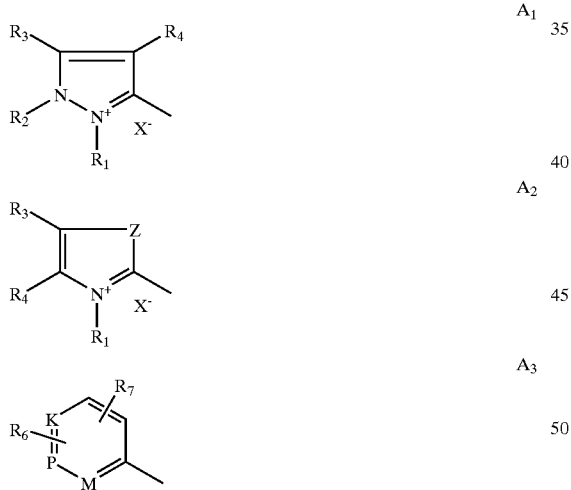

in which structures $A_1$ to $A_3$,
$R_1$ is chosen from $C_1$–$C_4$ alkyl radicals, a phenyl radical which can be substituted with a $C_1$–$C_4$ alkyl radical or a halogen atom chosen from chlorine, bromine, iodine and fluorine;
$R_2$ is chosen from $C_1$–$C_4$ alkyl radicals and a phenyl radical;
$R_3$ and $R_4$, which may be identical or different, are chosen from $C_1$–$C_4$ alkyl radicals, a phenyl radical or,
together form, in $A_1$, a benzene ring substituted with at least one radical chosen from $C_1$–$C_4$ alkyl radicals, $C_1$–$C_4$ alkoxy radicals and $NO_2$ radicals or, together form, in $A_2$, a benzene ring optionally substituted with at least one radical chosen from $C_1$–$C_4$ alkyl radicals, $C_1$–$C_4$ alkoxy radicals and $NO_2$ radicals;
$R_3$ can be further chosen from a hydrogen atom;
Z is chosen from an oxygen atom, a sulphur atom and —$NR_2$ radicals;
M is chosen from a —CH radical, —$C(C_1$–$C_4$ alkyl) radicals and —$N^+R_5(X^-)_r$ radicals;
K is chosen from a —CH radical, —$C(C_1$–$C_4$ alkyl) radicals and —$N^+R_5(X^-)_r$ radicals;
P is chosen from a —CH radical, —$C(C_1$–$C_4$ alkyl) radicals and —$N^+R_5(X^-)_r$ radicals;
wherein r denotes zero or 1;
wherein $R_5$ is chosen from an $O^-$ anion, $C_1$–$C_4$ alkoxy radicals and $C_1$–$C_4$ alkyl radicals;
$R_6$ and $R_7$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals, and —$NO_2$ radicals;
$X^-$ is chosen from anions;
with the proviso that,
wherein if $R_4$ is a $C_1$–$C_4$ alkyl radical and Z denotes a sulphur atom, $R_3$ is not a hydrogen atom;
wherein if $R_5$ is $O^-$, then r is zero;
wherein if K or P or M is —$N^+$—$(C_1$–$C_4$ alkyl)$X^-$, either $R_6$ or $R_7$ is not a hydrogen atom;
wherein if K is —$N^+R_5(X^-)_r$, M and P are the same and are chosen from a —CH radical and —$C(C_1$–$C_4$ alkyl) radicals;
wherein if M is —$N^+R_5(X^-)_r$, K and P are the same and are chosen from a —CH radical and —$C(C_1$–$C_4$ alkyl) radicals;
if P denotes —$N^+R_5(X^-)_r$, K and M are the same and are chosen from a —CH radical and —$C(C_1$–$C_4$ alkyl) radicals;
if Z is —$NR_2$ with $R_2$ being a radical chosen from $C_1$–$C_4$ alkyl radicals, at least one of the radicals $R_1$, $R_3$ or $R_4$ of $A_2$ is not chosen from $C_1$–$C_4$ alkyl radicals;
the symbol B is chosen from:
(a) a group of structure $B_1$ below:

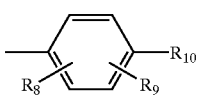

in which structure $B_1$,
$R_8$ is chosen from a hydrogen atom, a halogen atom chosen from chlorine, bromine, iodine and fluorine, $C_1$–$C_4$ alkyl radicals, $C_1$–$C_4$ alkoxy radicals, a radical —OH, a radical —$NO_2$, —$NHR_{11}$ radicals, —$NR_{12}R_{13}$ radicals, —NHCO ($C_1$–$C_4$) alkyl radicals, or forms with $R_9$ a 5- or 6-membered ring which may or may not contain at least one hetero atom chosen from nitrogen, oxygen and sulphur;
$R_9$ is chosen from a hydrogen atom, a halogen atom chosen from chlorine, bromine, iodine and fluorine, $C_1$–$C_4$ alkyl radicals, $C_1$–$C_4$ alkoxy radicals, or forms, with $R_{10}$ or $R_{11}$, a 5- or 6-membered ring which may or may not contain at least one hetero atom chosen from nitrogen, oxygen and sulphur;
$R_{10}$ is chosen from a hydrogen atom, an —OH radical, —$NHR_{11}$ radicals and —$NR_{12}R_{13}$ radicals;
$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;

R₁₂ and R₁₃, which may be identical or different, is chosen from $C_1$–$C_4$ alkyl radicals, $C_1$–$C_4$ monohydroxyalkyl radicals and $C_2$–$C_4$ polyhydroxyalkyl radicals;

(b) 5- and 6-membered nitrogenous heterocyclic groups optionally containing other heteroatoms or carbonyl groups and optionally substituted with at least one radical chosen from $C_1$–$C_4$ alkyl radicals, an amino radical, a phenyl radical, and wherein said at least one thickening polymer is chosen from polymers comprising:

(ii)₂—biopolysaccharide gums of microbial origin, except for xanthan gum;

(ii)₃—gums derived from plant exudates;

(ii)₄—pectins;

(ii)₅—alginates;

(ii)₆—starches; and (ii)₇—carboxyalkylcelluloses; and wherein said second composition comprises at least one oxidizing agent.

42. A ready-to-use composition for dyeing keratin fibers comprising: (i) at least one cationic dye chosen from compounds of the structures (I)₁ to (I)₇₇ below:

(I)₁

(I)₂

(I)₃

(I)₄

(I)₅

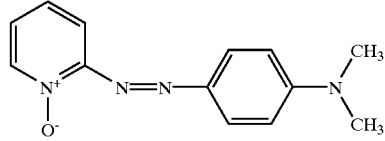

(I)₆

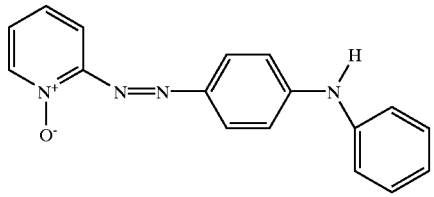

(I)₇

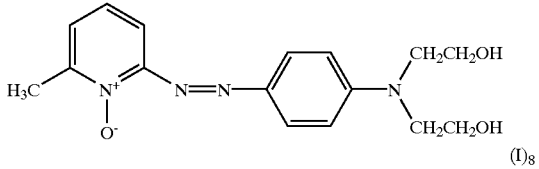

(I)₈

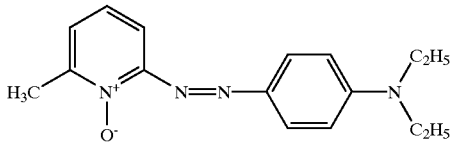

(I)₉

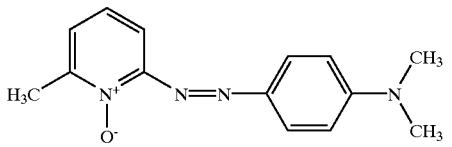

(I)₁₀

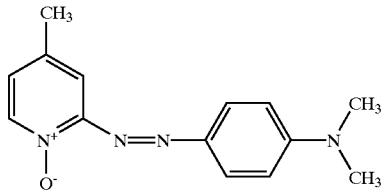

(I)₁₁

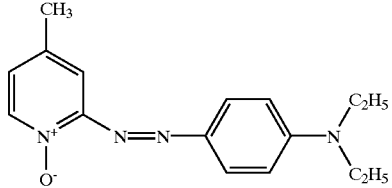

(I)₁₂

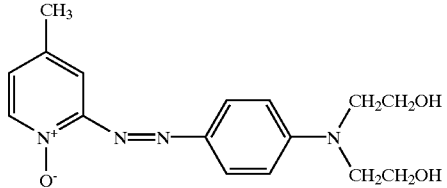

(I)₁₃

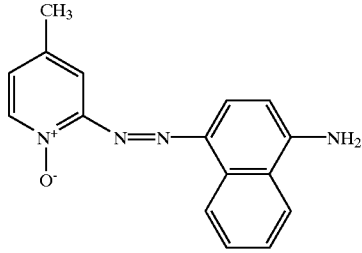

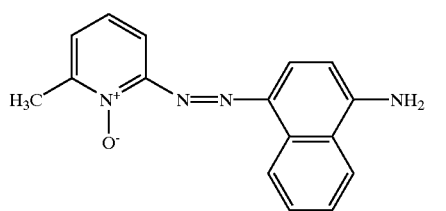
(I)14
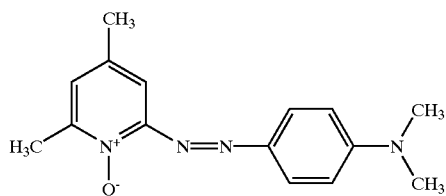
(I)15
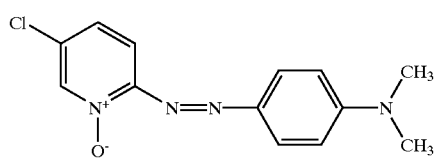
(I)16
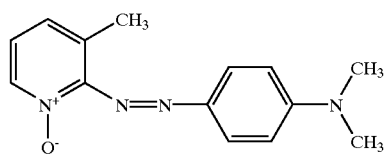
(I)17
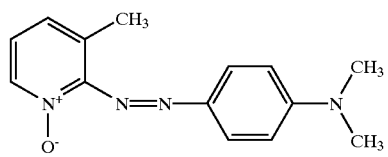
(I)17
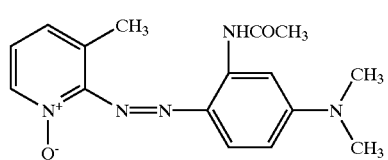
(I)18
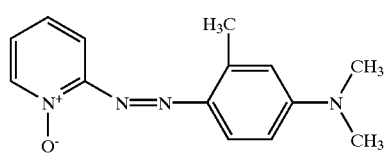
(I)19
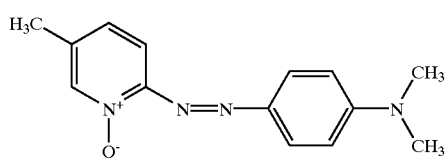
(I)20
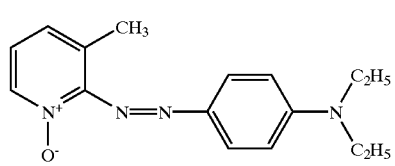
(I)21
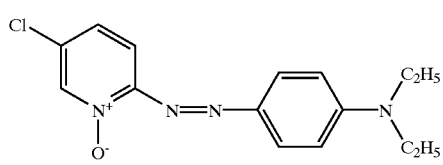
(I)22
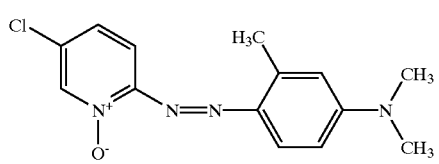
(I)23
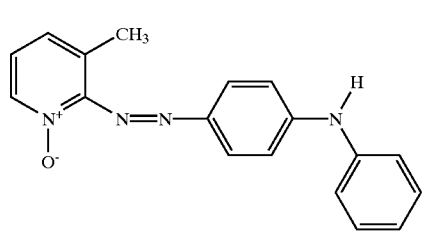
(I)24
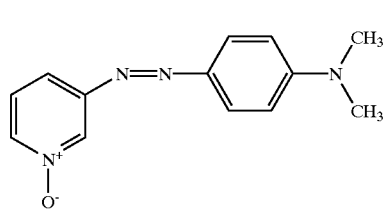
(I)25
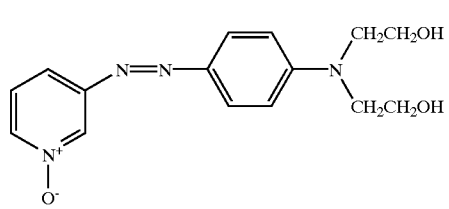
(I)26
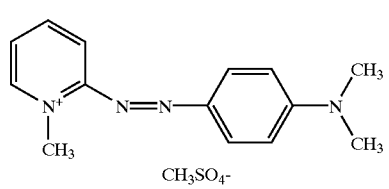
(I)27
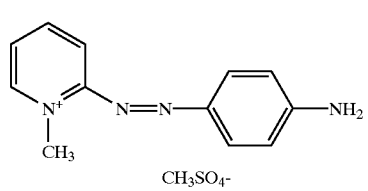
(I)28
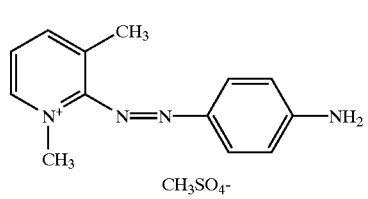
(I)29

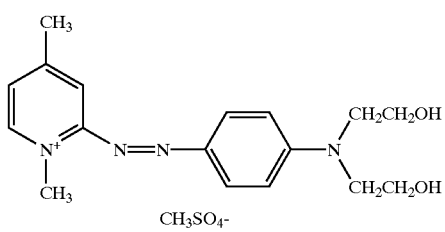
(I)30
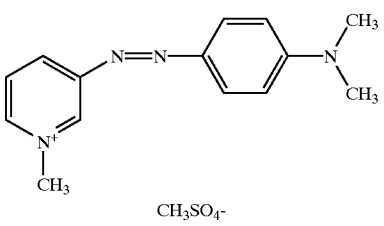
(I)37
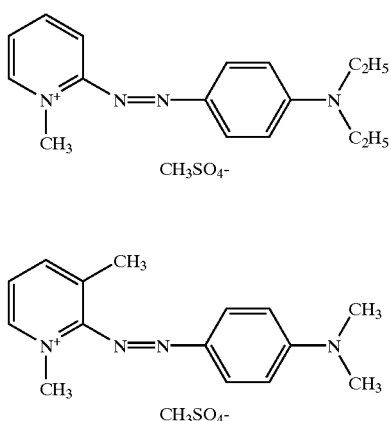
(I)31
(I)32
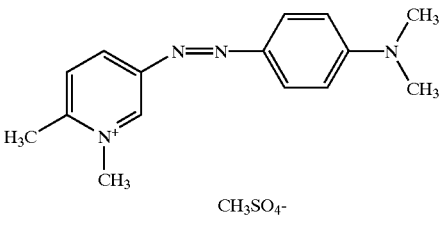
(I)38
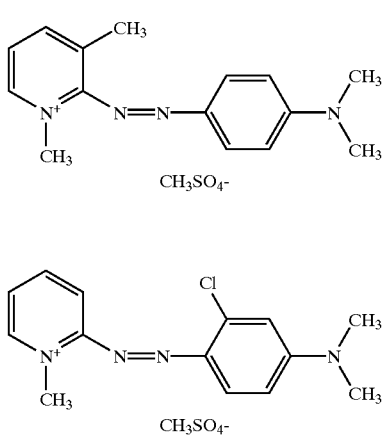
(I)33
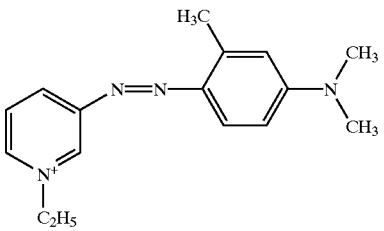
(I)39
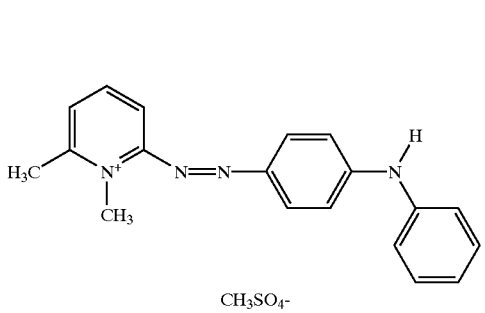
(I)34
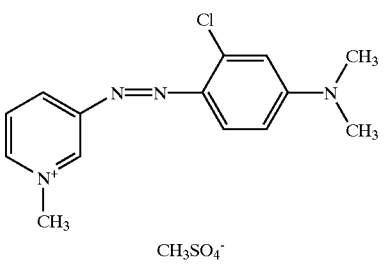
(I)40
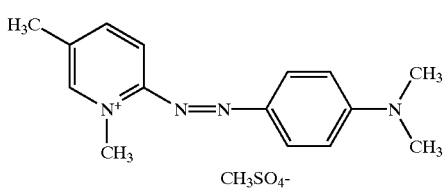
(I)35
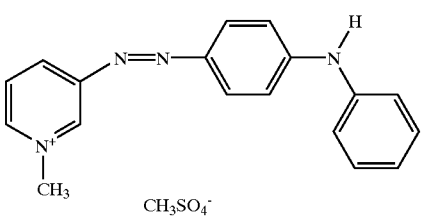
(I)41
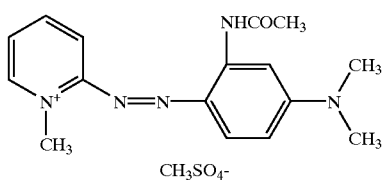
(I)36
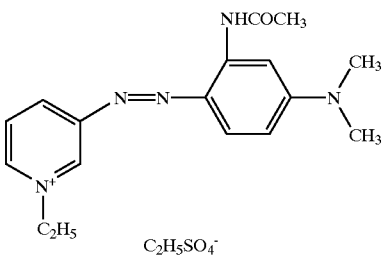
(I)42

-continued (I)₄₃

(I)₄₄

(I)₄₅

(I)₄₆

(I)₄₇

(I)₄₈

(I)₄₉

-continued (I)₅₀

(I)₅₁

(I)₅₂

(I)₅₃

(I)₅₄

(I)₅₅

(I)₅₆

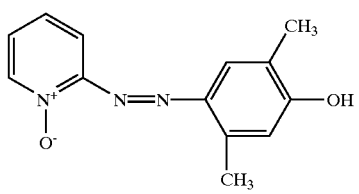 (I)57
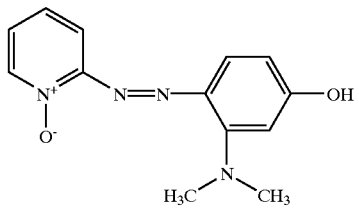 (I)58
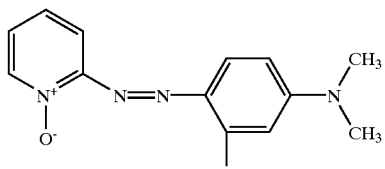 (I)59
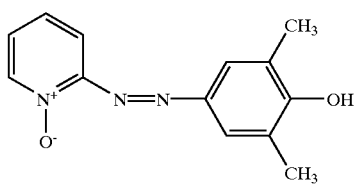 (I)60
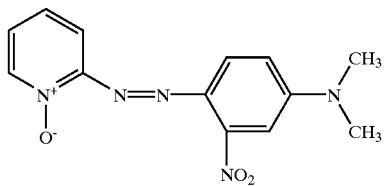 (I)61
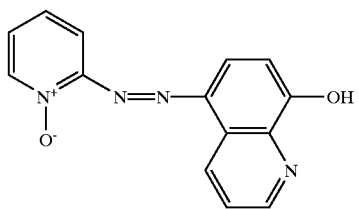 (I)62
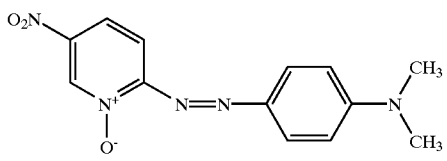 (I)63
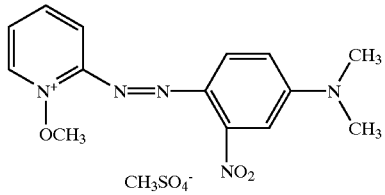 (I)64
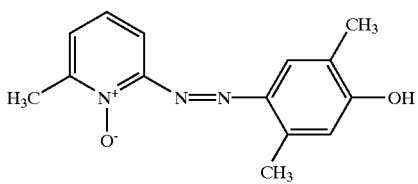 (I)65
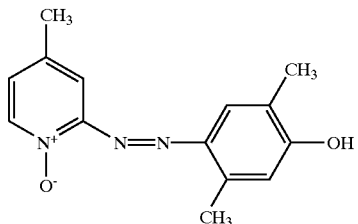 (I)66
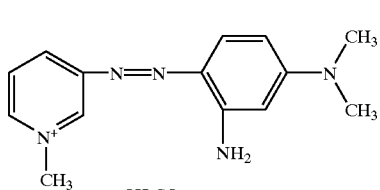 (I)67
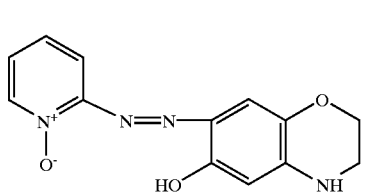 (I)68
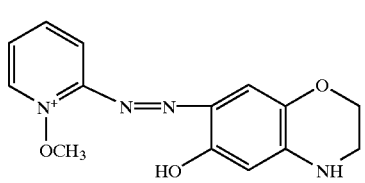 (I)69
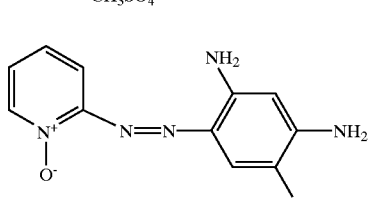 (I)70
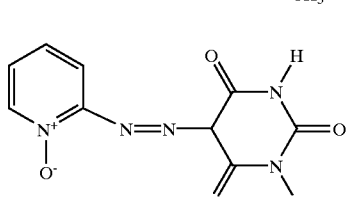 (I)71
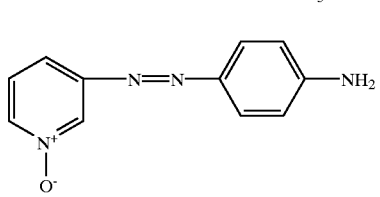 (I)72

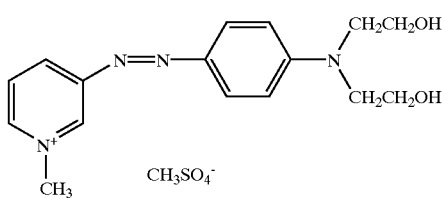
(I)₇₃
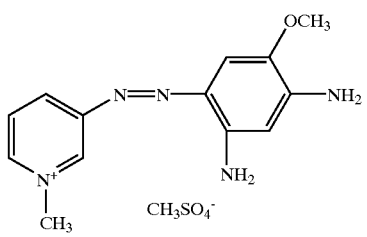
(I)₇₄
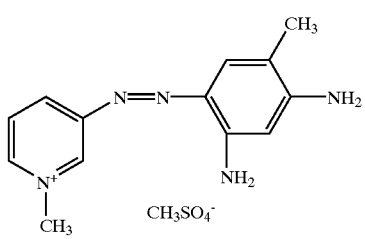
(I)₇₅
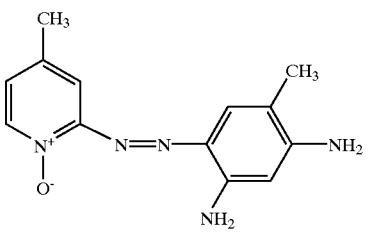
(I)₇₆
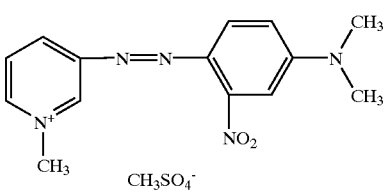
(I)₇₇
(ii) at least one thickening polymer chosen from polymers comprising:
- (ii)₂—biopolysaccharide gums of microbial origin, except for xanthan gum;
- (ii)₃—gums derived frorri plant exudates;
- (ii)₄—pectins;
- (ii)₅—alginates;
- (ii)₆—starches; and
- (ii)₇—carboxyalkylcelluloses.
\* \* \* \* \*

UNITED STATES PATENT AND TRADEMARK OFFICE
CERTIFICATE OF CORRECTION

PATENT NO.   : 6,613,102 B2                                    Page 1 of 2
DATED        : September 2, 2003
INVENTOR(S)  : Gérard Lang et al.

It is certified that error appears in the above-identified patent and that said Letters Patent is hereby corrected as shown below:

Column 20,
Line 1, " $N^+R_5(X^-)_r$," should read -- -$N^+R_5(X^-)_r$, --.
Line 2, "a-CH" should read -- a -CH --.
Line 66, "of structure of" should read -- of structure --.

Column 26,
Line 65, "below." should read -- below: --.

Column 27,
Lines 12-17, " 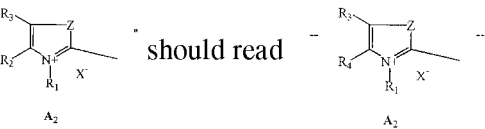 " should read 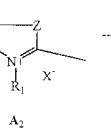 --.

Column 29,
Lines 12-17, " 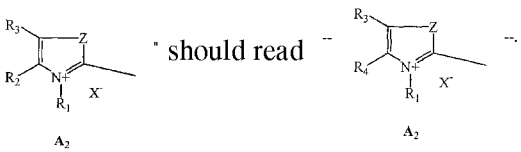 " should read 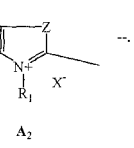 --.

Column 30,
Line 7, "bag" should read -- being --.

Column 31,
Lines 12-17, " 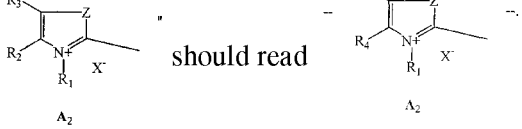 " should read 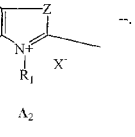 --.

Column 36,
Line 24, "a-CH" should read -- a -CH --.

Column 43,
Lines 33-39, delete the second occurrence of structure $(I)_{17}$.

UNITED STATES PATENT AND TRADEMARK OFFICE
CERTIFICATE OF CORRECTION

PATENT NO.    : 6,613,102 B2
DATED         : September 2, 2003
INVENTOR(S)   : Gérard Lang et al.

It is certified that error appears in the above-identified patent and that said Letters Patent is hereby corrected as shown below:

Column 52,
Line 24, "frorri" should read -- from --.

Signed and Sealed this

Thirtieth Day of December, 2003

JAMES E. ROGAN
*Director of the United States Patent and Trademark Office*